(12) United States Patent
Shtul et al.

(10) Patent No.: US 11,832,794 B2
(45) Date of Patent: Dec. 5, 2023

(54) SYSTEMS AND METHODS FOR CLEANING BODY CAVITIES

(71) Applicant: Motus GI Medical Technologies Ltd., Tirat HaCarmel (IL)

(72) Inventors: Boris Shtul, Kiryat-Motzkin (IL); Noam Hassidov, Moshav Bustan HaGalil (IL)

(73) Assignee: Motus GI Medical Technologies Ltd., Tirat HaCarmel (IL)

( * ) Notice: Subject to any disclaimer, the term of this patent is extended or adjusted under 35 U.S.C. 154(b) by 1071 days.

(21) Appl. No.: 16/571,265

(22) Filed: Sep. 16, 2019

(65) Prior Publication Data

US 2020/0023116 A1 Jan. 23, 2020

Related U.S. Application Data

(62) Division of application No. 13/703,986, filed as application No. PCT/IL2011/000470 on Jun. 13, 2011, now abandoned.

(Continued)

(51) Int. Cl.
*A61B 1/015* (2006.01)
*A61M 3/02* (2006.01)
(Continued)

(52) U.S. Cl.
CPC .............. *A61B 1/015* (2013.01); *A61B 1/126* (2013.01); *A61B 1/31* (2013.01); *A61M 1/777* (2021.05); *A61M 3/022* (2014.02); *A61M 3/0208* (2014.02); *A61M 3/0212* (2014.02); *A61M 3/0229* (2013.01); *A61M 3/0283* (2013.01);
(Continued)

(58) Field of Classification Search
CPC .... A61M 3/0208; A61M 3/011; A61M 3/012; A61M 1/006; A61M 1/777; A61M 1/85; A61M 1/77; A61M 3/0229; A61M 3/022; A61M 3/0212; A61M 3/0283; A61B 1/126; A61B 1/31; A61B 1/015; A61B 17/32037; A61B 2017/00296; A61B 2017/22037; A61B 1/0125; A61B 2017/32035
See application file for complete search history.

(56) References Cited

U.S. PATENT DOCUMENTS 3,735,751 A 5/1973 Katz
4,117,847 A 10/1978 Clayton
(Continued)

FOREIGN PATENT DOCUMENTS

AU 2005203844 7/2005
CN 1120805 4/1996
(Continued)

OTHER PUBLICATIONS

Official Action dated Jul. 2, 2014 From the US Patent and Trademark Office Re. U.S. Appl. No. 13/557,371.
(Continued)

*Primary Examiner* — Tiffany Legette

(57) ABSTRACT

This application presents methods and devices for continuously cleaning a colon by at least partially filling a segment of the colon with liquid and agitating the fluid to dislodge matter adhering to the colon walls. Methods for automatic maintenance of liquid levels in the colon during continuous cleaning are taught.

31 Claims, 19 Drawing Sheets

Related U.S. Application Data

(60) Provisional application No. 61/378,432, filed on Aug. 31, 2010, provisional application No. 61/354,226, filed on Jun. 13, 2010.

(51) Int. Cl.
*A61B 1/12* (2006.01)
*A61B 1/31* (2006.01)
*A61M 1/00* (2006.01)
*A61B 17/00* (2006.01)
*A61B 17/22* (2006.01)
*A61B 17/3203* (2006.01)

(52) U.S. Cl.
CPC ............ *A61B 17/32037* (2013.01); *A61B 2017/00296* (2013.01); *A61B 2017/22037* (2013.01); *A61M 1/77* (2021.05); *A61M 1/85* (2021.05); *A61M 3/0204* (2014.02); *A61M 2205/50* (2013.01); *A61M 2210/1064* (2013.01)

(56) References Cited

U.S. PATENT DOCUMENTS

| | | | |
|---|---|---|---|
| 4,257,422 A | 3/1981 | Duncan | |
| 4,445,509 A | 5/1984 | Auth | |
| 4,596,554 A | 6/1986 | Dastgeer | |
| 4,682,979 A | 7/1987 | Girouard | |
| 4,857,046 A | 8/1989 | Stevens et al. | |
| 4,874,363 A | 10/1989 | Abell | |
| 4,893,634 A | 1/1990 | Kulik et al. | |
| 4,902,276 A | 2/1990 | Zakko | |
| 5,019,056 A | 5/1991 | Lee et al. | |
| 5,047,040 A | 9/1991 | Simpson et al. | |
| 5,350,369 A | 9/1994 | Workman et al. | |
| 5,443,445 A | 8/1995 | Peters et al. | |
| 5,542,929 A | 8/1996 | Laabs et al. | |
| 5,630,795 A * | 5/1997 | Kuramoto | A61B 1/00137 604/35 |
| 5,782,747 A | 7/1998 | Zimmon | |
| 5,788,650 A | 8/1998 | Dotolo | |
| 6,106,506 A * | 8/2000 | Abell | F16K 7/07 604/257 |
| 6,149,581 A | 11/2000 | Klingenstein | |
| 6,500,142 B1 | 12/2002 | Harreld et al. | |
| 6,595,971 B1 | 7/2003 | Von Dyck et al. | |
| 6,984,226 B1 | 1/2006 | Abell et al. | |
| 8,065,772 B2 | 11/2011 | Maguire, Jr. et al. | |
| 8,075,539 B2 | 12/2011 | Nishtala et al. | |
| 2002/0045852 A1 | 4/2002 | Saab | |
| 2003/0176833 A1 | 9/2003 | Libermann | |
| 2005/0004533 A1 | 1/2005 | Smith | |
| 2005/0054996 A1 | 3/2005 | Gregory | |
| 2005/0070933 A1 | 3/2005 | Leiboff | |
| 2005/0085694 A1 | 4/2005 | Nakao | |
| 2005/0096503 A1 | 5/2005 | Conteas | |
| 2005/0119628 A1 | 6/2005 | Sant et al. | |
| 2005/0148954 A1 | 7/2005 | Abell | |
| 2005/0261553 A1 | 11/2005 | Swain et al. | |
| 2006/0009732 A1 * | 1/2006 | Hardy | A61M 3/0275 604/35 |
| 2006/0025728 A1 | 2/2006 | Leiboff et al. | |
| 2006/0025729 A1 | 2/2006 | Leiboff et al. | |
| 2006/0173244 A1 * | 8/2006 | Boulais | A61B 1/015 600/156 |
| 2007/0015965 A1 | 1/2007 | Cox et al. | |
| 2007/0078444 A1 | 4/2007 | Larsson | |
| 2007/0244520 A1 | 10/2007 | Ferren et al. | |
| 2008/0014622 A1 * | 1/2008 | Federspiel | B01D 67/0093 435/182 |
| 2008/0097292 A1 | 4/2008 | Cabiri et al. | |
| 2008/0167606 A1 * | 7/2008 | Dann | A61F 5/0076 604/95.04 |
| 2008/0255596 A1 | 10/2008 | Jenson et al. | |
| 2008/0262308 A1 * | 10/2008 | Prestezog | A61B 1/015 600/156 |
| 2009/0143722 A1 | 6/2009 | Kim | |
| 2009/0264910 A1 | 10/2009 | Laufer | |
| 2010/0049119 A1 * | 2/2010 | Norman | A61M 3/022 604/31 |
| 2010/0256447 A1 | 10/2010 | Dubi et al. | |
| 2011/0160657 A1 | 6/2011 | Gobel | |
| 2012/0253284 A1 | 10/2012 | Nitsan et al. | |
| 2012/0289892 A1 | 11/2012 | Shtul et al. | |
| 2012/0289910 A1 | 11/2012 | Shtul et al. | |
| 2013/0066297 A1 | 3/2013 | Shtul et al. | |
| 2013/0085442 A1 | 4/2013 | Shtul et al. | |
| 2013/0296771 A1 | 11/2013 | Shtul et al. | |

FOREIGN PATENT DOCUMENTS

| | | |
|---|---|---|
| CN | 1868554 | 11/2006 |
| CN | 101607100 | 12/2009 |
| DE | 8904403 | 7/1989 |
| EP | 1262205 | 12/2002 |
| EP | 2529779 | 12/2012 |
| JP | 02-191464 | 7/1990 |
| JP | 05-161711 | 6/1993 |
| JP | 2003-010324 | 1/2003 |
| WO | WO 88/00840 | 2/1988 |
| WO | WO 92/17219 | 10/1992 |
| WO | WO 94/18894 | 9/1994 |
| WO | WO 99/60934 | 12/1999 |
| WO | WO 2006/039511 | 4/2006 |
| WO | WO 2006/086826 | 8/2006 |
| WO | WO 2008/093288 | 8/2008 |
| WO | WO 2009/125387 | 10/2009 |
| WO | WO 2009/143201 | 11/2009 |
| WO | WO 2011/083450 | 7/2011 |
| WO | WO 2011/083451 | 7/2011 |
| WO | WO 2011/158232 | 12/2011 |

OTHER PUBLICATIONS

Official Action dated Jun. 2, 2016 From the US Patent and Trademark Office Re. U.S. Appl. No. 13/557,363.
Official Action dated Sep. 5, 2018 From the US Patent and Trademark Office Re. U.S. Appl. No. 13/703,986. (38 pages).
Official Action dated Nov. 6, 2013 From the US Patent and Trademark Office Re. U.S. Appl. No. 13/557,371.
Official Action dated Jan. 11, 2019 From the US Patent and Trademark Re. U.S. Appl. No. 13/557,363. (11 pages).
Official Action dated Feb. 13, 2017 From the US Patent and Trademark Office Re. U.S. Appl. No. 13/703,986. (31 pages).
Official Action dated Jul. 13, 2018 From the US Patent and Trademark Office U.S. Appl. No. 13/557,363. (30 pages).
Official Action dated Apr. 15, 2016 From the US Patent and Trademark Office Re. U.S. Appl. No. 13/521,483.
Official Action dated Dec. 15, 2014 From the US Patent and Trademark Office Re. U.S. Appl. No. 13/521,061.
Official Action dated Dec. 15, 2016 From the US Patent and Trademark Office Re. U.S. Appl. No. 13/557,363. (29 pages).
Official Action dated May 15, 2019 From the US Patent and Trademark Office Re. U.S. Appl. No. 13/703,986. (17 pages).
Official Action dated Sep. 15, 2015 From the US Patent and Trademark Office Re. U.S. Appl. No. 13/557,371.
Official Action dated Sep. 15, 2017 From the US Patent and Trademark Office Re. U.S. Appl. No. 13/557,363. (27 pages).
Official Action Dated Jan. 17, 2017 From the US Patent and Trademark Office Re. U.S. Appl. No. 13/557,371. (34 pages).
Official Action dated Oct. 17, 2016 From the US Patent and Trademark Office Re. U.S. Appl. No. 13/521,483.
Official Action dated Jun. 21, 2018 From the US Patent and Trademark Office Re. U.S. Appl. No. 13/521,483. (16 pages).
Official Action dated May 21, 2014 From the US Patent and Trademark Office Re. U.S. Appl. No. 13/521,061.
Official Action dated Jun. 23, 2016 From the US Patent and Trademark Office Re. U.S. Appl. No. 13/703,986.

(56) References Cited

OTHER PUBLICATIONS

Official Action dated Aug. 24, 2017 From the US Patent and Trademark Office Re. U.S. Appl. No. 13/703,986. (18 pages).
Official Action dated Mar. 24, 2016 From the US Patent and Trademark Office Re. U.S. Appl. No. 13/521,061.
Official Action dated Mar. 24, 2016 From the US Patent and Trademark Office Re. U.S. Appl. No. 13/557,371.
Official Action dated Oct. 26, 2017 From the US Patent and Trademark Office Re. U.S. Appl. No. 13/521,483. (38 pages).
Official Action dated Jun. 29, 2017 From the US Patent and Trademark Office Re. U.S. Appl. No. 13/557,371. (34 pages).
Official Action dated Dec. 30, 2015 From the US Patent and Trademark Office Re. U.S. Appl. No. 13/703,986.
Official Action dated Dec. 30, 2016 From the US Patent and Trademark Office Re. U.S. Appl. No. 13/521,061. (31 pages).
Decision of Rejection dated Feb. 2, 2016 From the Japanese Patent Office Re. Application No. 2013-514838 and Its Translation Into English.
Restriction Official Action dated Nov. 16, 2015 From the US Patent and Trademark Office Re. U.S. Appl. No. 13/557,363.
Restriction Official Action dated Dec. 19, 2013 From the US Patent and Trademark Office Re. U.S. Appl. No. 13/521,061.
Restriction Official Action dated Nov. 23, 2015 From the US Patent and Trademark Office Re. U.S. Appl. No. 13/521,483.
Restriction Official Action dated Jun. 26, 2015 From the US Patent and Trademark Office Re. U.S. Appl. No. 13/703,986.
Supplementary European Search Report and the European Search Opinion dated Mar. 29, 2017 From the European Patent Office Re. Application No. 11731727.1. (9 Pages).
Translation dated Dec. 10, 2014 of Notification of Office Action and Search Report dated Nov. 24, 2014 From the State Intellectual Property Office of the People's Republic of China Re. Application No. 201180039602.2.
Advisory Action Before the Filing of an Appeal Brief dated Jan. 6, 2017 From the US Patent and Trademark Office Re. U.S. Appl. No. 13/521,483. (4 pages).
Advisory Action Before the Filing of an Appeal Brief dated Feb. 22, 2018 From the US Patent and Trademark Office Re. U.S. Appl. No. 13/703,986. (3 pages).
Applicant-Initiated Interview Summary dated Dec. 2, 2016 From the US Patent and Trademark Office Re. U.S. Appl. No. 13/521,483. (3 pages).
Applicant-Initiated Interview Summary dated Feb. 3, 2017 From the US Patent and Trademark Office Re. U.S. Appl. No. 13/557,363. (4 pages).
Applicant-Initiated Interview Summary dated Nov. 7, 2016 From the US Patent and Trademark Office Re. U.S. Appl. No. 13/703,986. (3 pages).
Applicant-Initiated Interview Summary dated Apr. 13, 2017 From the US Patent and Trademark Office Re. U.S. Appl. No. 13/703,986. (3 pages).
Applicant-Initiated Interview Summary dated Nov. 14, 2014 From the US Patent and Trademark Office Re. U.S. Appl. No. 13/557,371.
Applicant-Initiated Interview Summary dated Feb. 16, 2017 From the US Patent and Trademark Office Re. U.S. Appl. No. 13/557,371. (4 pages).
Applicant-Initiated Interview Summary dated Jun. 19, 2019 From the US Patent and Trademark Office Re. U.S. Appl. No. 13/703,986. (7pages).
Applicant-Initiated Interview Summary dated Mar. 20, 2015 From the US Patent and Trademark Office Re. U.S. Appl. No. 13/521,061.
Applicant-Initiated Interview Summary dated Mar. 21, 2017 From the US Patent and Trademark Office Re. U.S. Appl. No. 13/557,363. (6 pages).
Applicant-Initiated Interview Summary dated Aug. 29, 2018 From the US Patent and Trademark Office Re. U.S. Appl. No. 13/521,483. (3 pages).
Applicant-Initiated Interview Summary dated Aug. 31, 2018 From the US Patent and Trademark Office Re. U.S. Appl. No. 13/557,363. (3 pages).

Communication Pursuant to Article 94(3) EPC dated Jul. 5, 2016 From the European Patent Office Re. Application No. 11703037.9.
Communication Pursuant to Article 94(3) EPC dated Jul. 12, 2016 From the European Patent Office Re. Application No. 11732520.9.
Communication Pursuant to Article 94(3) EPC dated Sep. 25, 2018 From the European Patent Office Re. Application No. 11731727.1. (6 Pages).
Communication Relating to the Results of the Partial International Search dated Jun. 6, 2011 From the International Searching Authority Re. Application No. PCT/IB2011/050121.
Communication Relating to the Results of the Partial International Search dated Nov. 15, 2011 From the International Searching Authority Re. Application No. PCT/IL2011/000470.
Examination Report dated Jul. 17, 2014 From the Instituto Mexicano de la Propiedad Industrial Re. Application No. Mx/a/2012/008056 and Its Translation Into English.
Examination Report Under Sections 12 & 13 of the Patents Act, 1970 and the Patents Rules, 2003 dated Jun. 21, 2019 From the Government of India, Intellectual Property India, Patents, Designs, Trade Marks, Geographical Indications Re. Application No. 1700/MUMNP/2012. (5 Pages).
international Preliminary Report on Patentability dated Jul. 26, 2012 From the International Bureau of WIPO Re. Application No. PCT/IB2011/050120.
International Preliminary Report on Patentability dated Jul. 26, 2012 From the International Bureau of WIPO Re. Application No. PCT/IB2011/050121.
International Preliminary Report on Patentability dated Dec. 27, 2012 From the International Bureau of WIPO Re. Application No. PCT/IL2011/000470.
International Search Report and the Written Opinion dated Feb. 17, 2012 From the International Searching Authority Re. Application No. PCT/IL2011/000470.
International Search Report and the Written Opinion dated Aug. 18, 2011 From the International Searching Authority Re. Application No. PCT/1B2011/050121.
International Search Report and the Written Opinion dated Aug. 26, 2011 From the International Searching Authority Re. Application No. PCT/IB2011/050120.
Invitation to Pay Additional Fees dated Jun. 22, 2011 From the International Searching Authority Re. Application No. PCT/IB2011/050120.
Notice of Reason for Rejection dated Dec. 1, 2017 From the Japan Patent Office Re. Application No. 2016-110785 and Its Translation Into English.
Notice of Reason for Rejection dated Nov. 7, 2014 From the Japanese Patent Office Re. Application No. 2012-548515 and Its Translation Into English.
Notice of Reason for Rejection dated Mar. 20, 2015 From the Japanese Patent Office Re. Application No. 2013-514838 and Its Translation Into English.
Notice of Reason for Rejection dated Mar. 23, 2018 From the Japan Patent Office Re. Application No. 2016-110785 and Its Translation Into English. (4 Pages).
Notice of Reason for Rejection dated Mar. 31, 2017 From the Japan Patent Office Re. Application No. 2016-110785 and Its Translation Into English. (8 Pages).
Notification of Office Action and Search Report dated Nov. 24, 2014 From the State Intellectual Property Office of the People's Republic of China Re. Application No. 201180039602.2.
Notification of Office Action dated Apr. 2, 2014 From the State Intellectual Property Office of the People's Republic of China Re. Application No. 201180039602.2 and Its Translation Into English.
Office Action and Search Report dated Oct. 10, 2014 From the State Intellectual Property Office of the People's Republic of China Re. Application No. 201180013505.6 and Its Translation Into English.
Office Action and Search Report dated Jan. 17, 2014 From the State Intellectual Property Office of the People's Republic of China Re. Application No. 201180013505.6 and Its Summary in English.
Official Action dated Jan. 11, 2019 From the US Patent and Trademark Office Re. U.S. Appl. No. 13/557,363. (11 pages).
Official Action dated Jul. 13, 2018 From the US Patent and Trademark Office Re. U.S. Appl. No. 13/557,363. (30 pages).

(56) References Cited

OTHER PUBLICATIONS

Official Action dated Oct. 17, 2016 From the US Patent and Trademark Re. U.S. Appl. No. 13/521,483.
Official Action dated Oct. 26, 2017 From the US Patent and Trademark Re. U.S. Appl. No. 13/521,483. (38 pages).
Official Action dated Jun. 29, 2017 From the US Patent and Trademark Office U.S. Appl. No. 13/557,371. (34 pages).
Supplementary European Search Report and the European Search Opinion dated Mar. 29, 2017 From the European Patent Office Re. Application No. 11731727.1.

* cited by examiner

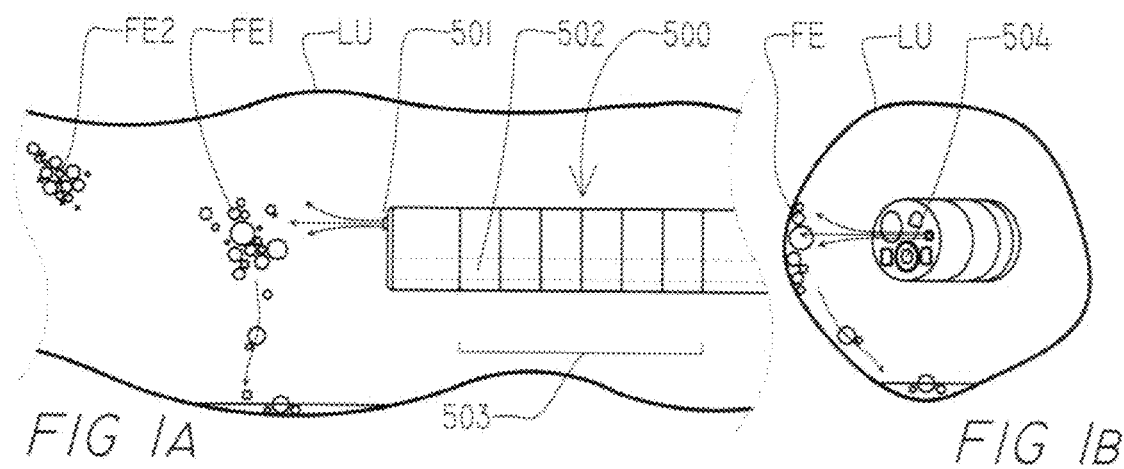
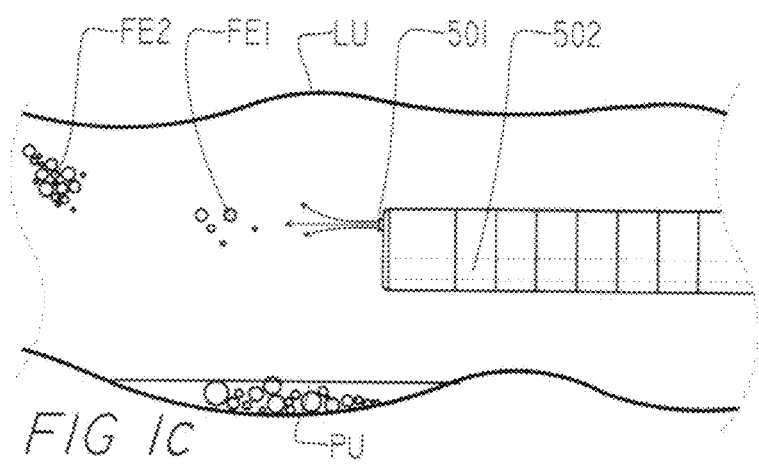
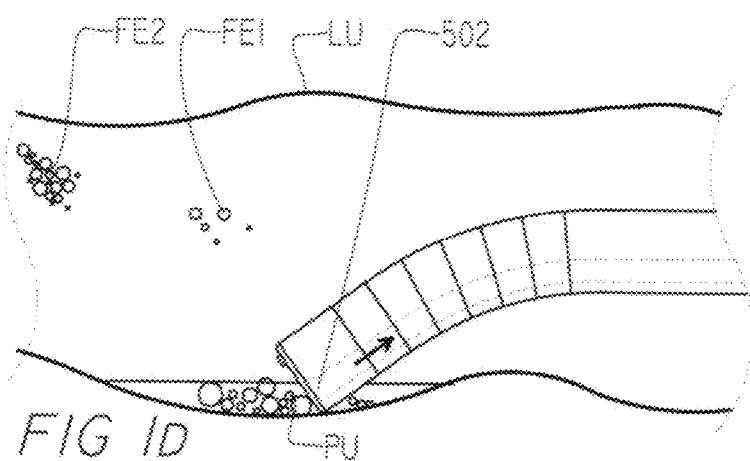

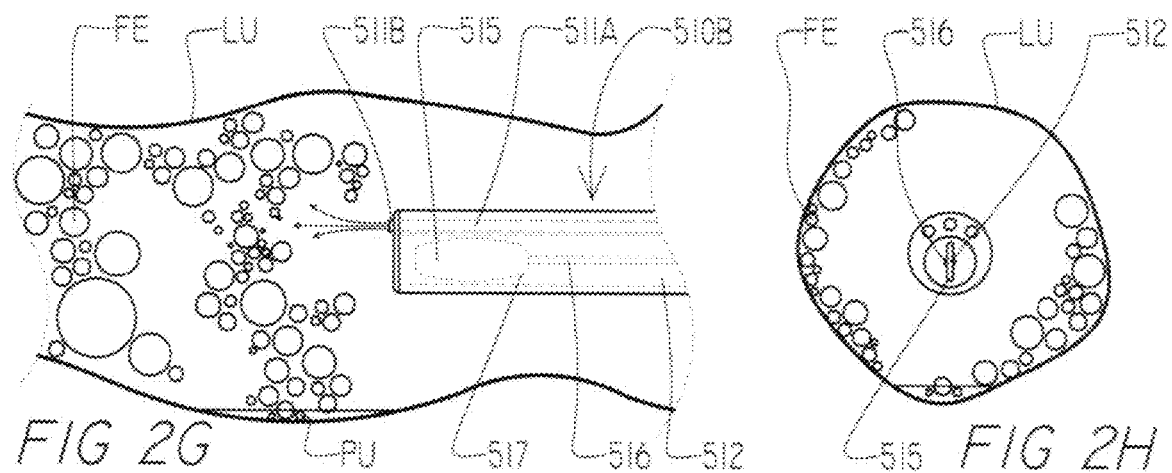
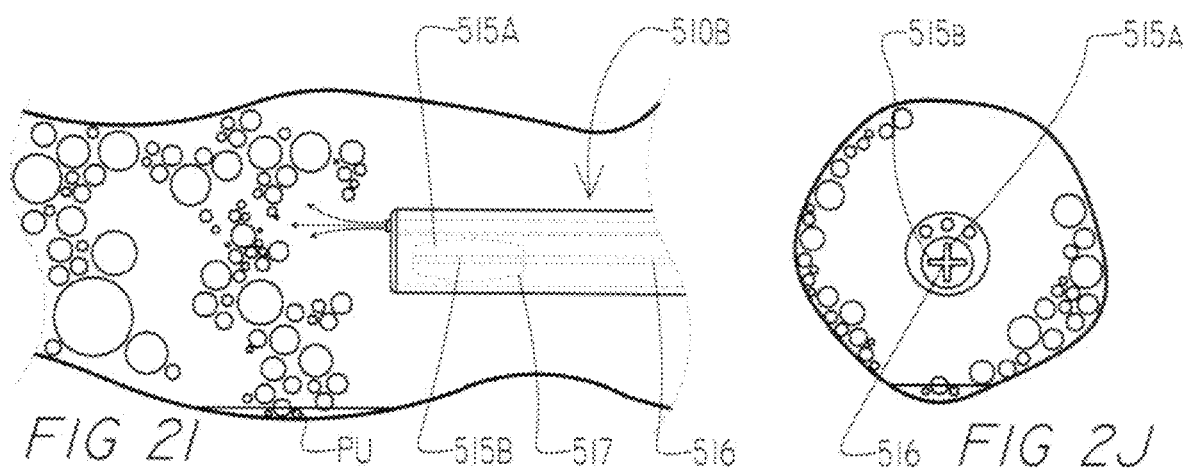

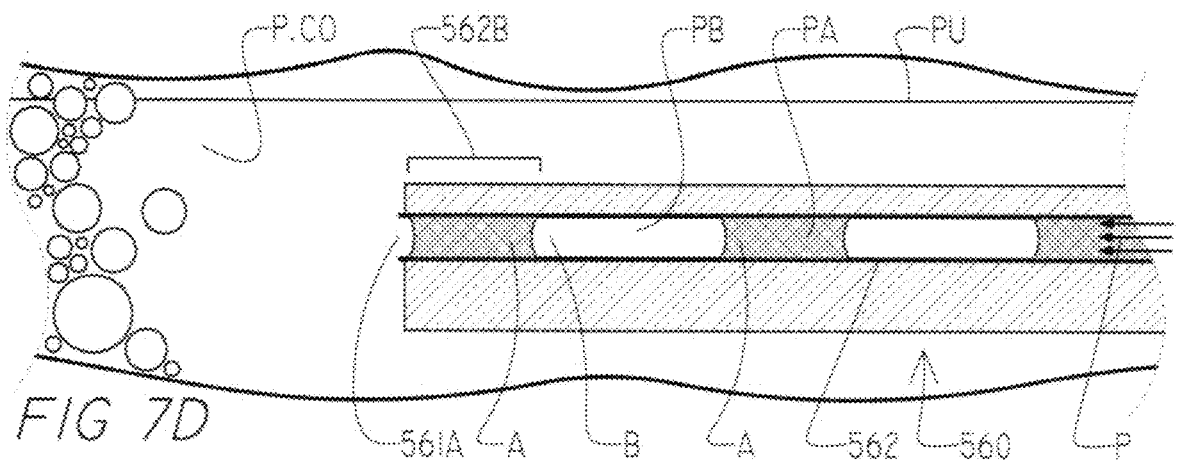
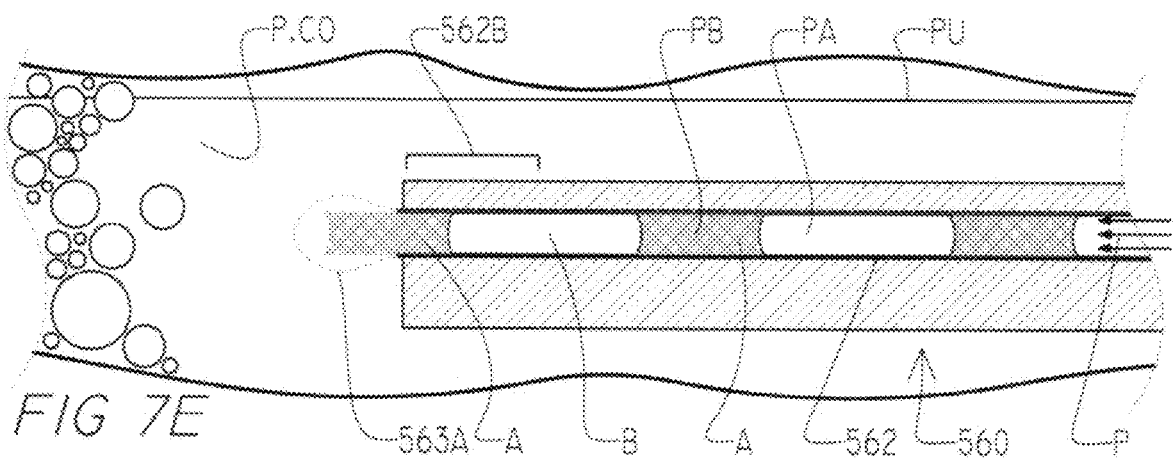
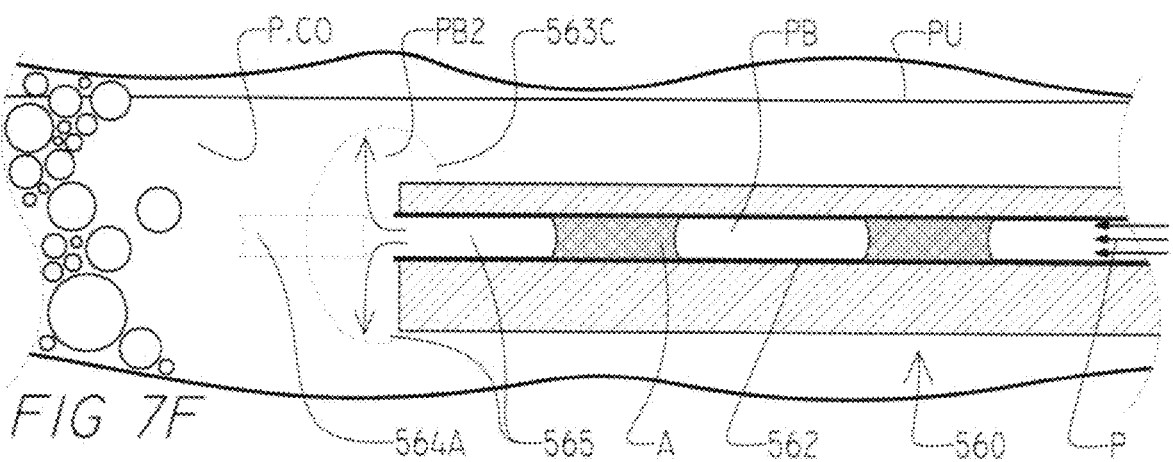

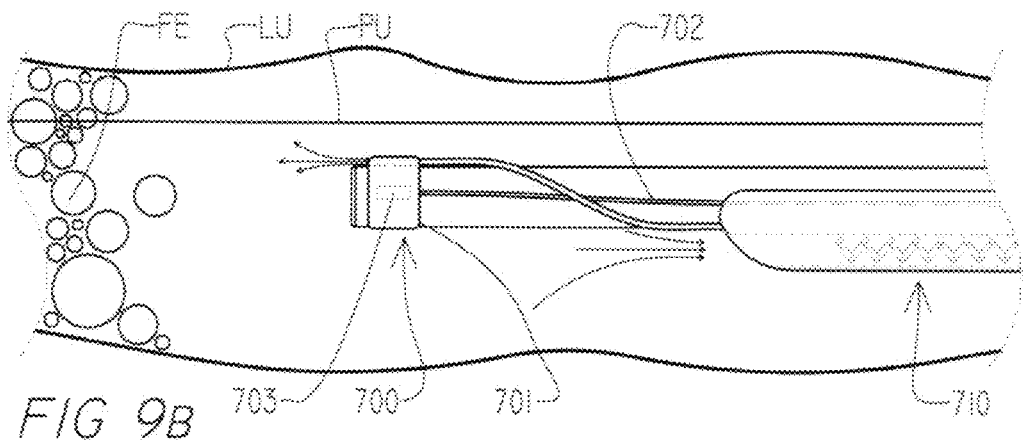
FIG 9B
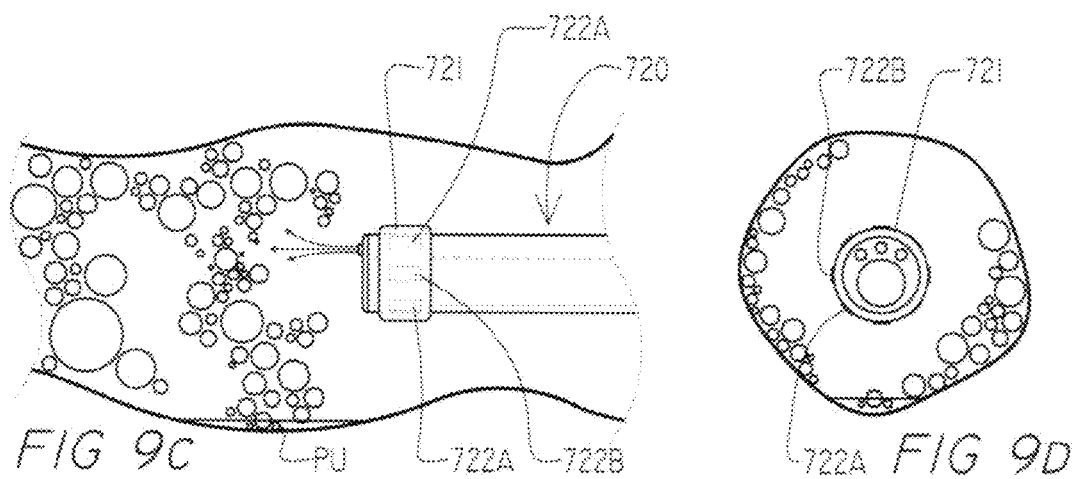
FIG 9C
FIG 9D
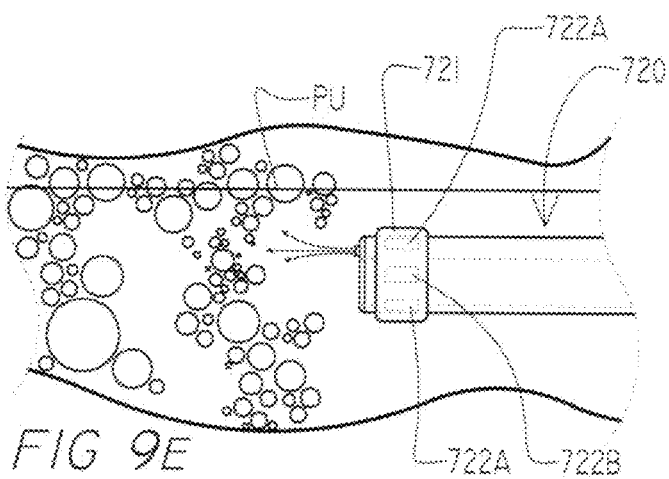
FIG 9E

SYSTEMS AND METHODS FOR CLEANING BODY CAVITIES

RELATED APPLICATIONS

This application is a division of U.S. patent application Ser. No. 13/703,986 filed on Dec. 13, 2012, which is a National Phase of PCT Patent Application No. PCT/IL2011/000470 having International Filing Date of Jun. 13, 2011, which claims the benefit of priority under 35 USC § 119(e) of U.S. Provisional Patent Application Nos. 61/354,226 filed on Jun. 13, 2010 and 61/378,432 filed on Aug. 31, 2010. The contents of the above applications are all incorporated by reference as if fully set forth herein in their entirety.

FIELD AND BACKGROUND OF THE INVENTION

The present invention, in some embodiments thereof, relates to devices and methods for cleaning body cavities and, more particularly, but not exclusively, to devices and methods for cleaning a human colon.

Use of an enema for cleaning a portion of the colon has been known for many centuries. Enemas typically insert water into the rectum through a short nozzle, and clean up to about 60 cm of the lower colon, the sigmoid colon. "Hydrotheraphy" systems using a short nozzle that inserts purified water in to the human colon as high as the cecum (150-180 cm) can clean the entire colon. This process takes up to one hour per session and in some cases several cleansing sessions are needed. The process can be uncomfortable and inconvenient for that reason. Early attempts to insert long flexible tubes into the colon to enhance the cleansing process, without a camera or other visual guidance system and often practiced by operators without proper training, were found to damage the colon walls, sometimes causing fatal perforations.

Patients requiring endoscopic observation of the colon undergo pharmacological (laxative) colon preparation prior to the endoscopic exam, using agents that generate massive bowel movements. However, by one current estimate such preparation is found to effectively cleanse the colon wall in only about 75% of the patients who use it.

In an additional recent and contemporary practice, an endoscope (colonoscopy) is inserted in the lower intestine and is used to clean the colon as well as to observe the colon after cleaning. A colonoscope typically comprises a camera for viewing the intestinal cavity, a pressurized water delivery system for aiming a stream of water at a concentration of fecal matter visible through the camera, and a suction device which may be directed towards a portion of fecal matter dislodged from the intestinal wall so as to aspirate the dislodged matter and transport it out of the body. Various devices fitting this description are well known in the art, and are used to prepare the colon for diagnostic visual inspection by a surgeon.

In a typical procedure, when a GI physician using a colonoscope encounters fecal matter blocking the colonoscope view, he may steer the colonoscope tip until he has a good view of the fecal matter via the colonoscope's onboard camera, and will then inject water to dislodge the fecal matter, and then aspirate the dissolved fecal matter out of the body. Auxiliary pumps are sometimes used to generate high vacuum levels and powerful water jets. Internal lumens of the colonoscope may be used for inputting water and outputting fecal matter, or a multi-lumen external apparatus may be attached to the colonoscope to provide high throughput and to free the colonoscope's working channel(s) for other tasks. PCT application WO2009/143201 (Gordon et al.) teaches a system of this type. Alternatively, use of a special nozzle to produce high water pressure at the distal tip of a colonoscope working channel is taught in PCT Application WO2009/125387 (by Nitsan et al).

SUMMARY OF THE INVENTION

The present invention, in some of its embodiments, provides methods and devices for more effective cleaning of the colon or other body cavities, which methods and devices require less operator effort, are faster, and are more effective than methods of prior art.

There is provided in accordance with an exemplary embodiment of the invention a device for continuously cleaning a colon comprising:
a. a fluid input tube for supplying fluid to a colon segment being cleaned;
b. a material output tube through which liquid and fecal matter may be removed from the colon; and
c. a controller configured to establish and maintain a condition while continuously cleaning, in which the colon segment being cleaned is mostly filled with a mixture of the liquid and the fecal matter.

In an exemplary embodiment of the invention, mostly filled comprises at least 60% filled.

In an exemplary embodiment of the invention, the controller is programmed to maintain within the colon segment a liquid fill level such that a distal end of the device is fully submerged in the mixture.

In an exemplary embodiment of the invention, the maintain comprises maintaining the mostly filled colon segment according to changes in dimensions of the colon segment.

In an exemplary embodiment of the invention, the colon segment comprises a volume of 50 mL to 500 mL.

In an exemplary embodiment of the invention, the continuously cleaning comprises at least one of an exchange of fluid between the device and the colon segment and agitation of the fluid.

In an exemplary embodiment of the invention, the cleaning comprises removing feces at least 5 cm distal to the device.

In an exemplary embodiment of the invention, the controller is configured to control at least one of
a supply of liquid through the fluid input tube, and
a flow of matter through the output tube, wherein the supply and the flow comprise a range of between 400 cc/min and 2000 cc/min.

In an exemplary embodiment of the invention, the device further comprises an agitator for agitating the mixture, wherein the agitator transfers an amount of energy sufficient to at least one of dislodge fecal matter from a wall of the colon and break-down relatively large fecal matter into relatively smaller fecal matter. Optionally, the material output tube comprises the agitator. Optionally, the agitator comprises a fluid flow pulsator which alternates delivery of liquid within the input tube and delivery of gas within the input tube, wherein a pressure of the gas is at least 0.2 ATM above a pressure of the liquid. Optionally, the fluid input tube comprises the fluid flow pulsator. Alternatively or additionally, the agitator comprises a rotating element comprised within the output tube. Alternatively or additionally, the agitator comprises a vibration element for inducing vibration in the mixture. Alternatively or additionally, the agitator comprises a plurality of nozzles, the nozzles are offset from a longitudinal axis of the device, the nozzles positioned and aimed to induce a rotational movement in the mixture.

In an exemplary embodiment of the invention, the device further comprises a size-reducer for reducing size of the fecal matter passing into and through the output tube.

In an exemplary embodiment of the invention, the controller is programmed to control at least one of input flow and output flow in such a way that a pressure change inside the colon segment does not exceed 0.06 Bar above an ambient pressure.

In an exemplary embodiment of the invention, the controller is programmed to control at least one of input flow and output flow in such a way that a pressure change inside the colon segment and proximate to a distal end of the device does not fall 0.20 Bar below an ambient pressure.

In an exemplary embodiment of the invention, the controller is programmed to control at least one of input flow and output flow in such a way that pressure inside the colon segment and proximate to a distal end of the device is maintained within a range of 30 mbar-76 mbar.

In an exemplary embodiment of the invention, the device cleans at least 90% of feces from the colon segment while advancing in the colon at least at 10 cm per minute.

In an exemplary embodiment of the invention, the device is an add-on to a colonoscope.

In an exemplary embodiment of the invention, the device further comprises a filter coupled to the outlet tube, wherein an opening to the outlet tube is larger than openings in the filter. Optionally, the filter comprises a plurality of openings substantially parallel to a direction of motion of the device, wherein the motion of device inside the colon dislodges feces trapped in the openings.

In an exemplary embodiment of the invention, the material output tube further comprises:
 a) plurality of lobes running side by side and in fluid communication with each other along at least a portion of a length of the material output tube; and
 b) at least one rotatable device housed in one of the lobes and free to rotate within the lobe, but prevented by shape of the lobe from moving laterally into another of the plurality of lobes. Optionally, the material output tube further comprises:
 a) a first helical device positioned within a first lobe of the output tube;
 b) a second helical device positioned within a second lobe of the output tube; and
 c) a mechanism for rotating the first and the second helical devices in tandem.

In an exemplary embodiment of the invention, the device further comprises a memory coupled to the controller, the memory comprising a table correlating at least one cleaning parameter with at least one other parameter.

There is provided in accordance with an exemplary embodiment of the invention a method of cleaning a colon comprising advancing at a speed greater than 10 cm per minute a distal end of a cleaning device, which distal end removes more than 95% of feces initially contained within colon segments within which the device advances.

There is provided in accordance with an exemplary embodiment of the invention a method for cleaning a colon, comprising:
 filling a volume of a segment of the colon with a liquid to be mostly full;
 agitating a mixture of the liquid and feces;
 inserting additional liquid into the colon segment while simultaneously removing the mixture from the colon segment to maintain a condition in which the colon segment is mostly full; and
 emptying the liquid from the segment.

In an exemplary embodiment of the invention, mostly full comprises at least 60% full of the mixture.

In an exemplary embodiment of the invention, maintaining comprises maintaining the mostly full state according to changes in dimensions of the colon segment.

In an exemplary embodiment of the invention, agitating comprises applying an amount of energy to the mixture in an omni-directional manner. Optionally, agitating comprises transferring a sufficient amount of energy to at least one of dislodge fecal matter from at least some of the surface area of walls of the segment and break-down at least some of the volume of relatively large fecal matter blocks inside the segment. Optionally, transferring a sufficient amount of energy comprises transferring a sufficient amount of energy at least 10 cm from an agitation device to the mixture.

In an exemplary embodiment of the invention, the method further comprises progressively advancing a colon cleaning device along a length of the colon at a rate of at least 10 cm/second while maintaining the volume of the segment.

In an exemplary embodiment of the invention, the method further comprises maintaining a pressure of the liquid in the colon segment within a range of 30-76 mbar during the inserting and the simultaneous removing.

In an exemplary embodiment of the invention, the method further comprises maintaining an ambient pressure of the liquid in the colon segment during the inserting and the simultaneous removing within at least one of an increase in the ambient pressure of no more than 0.06 Bar and a decrease in the ambient pressure of no more than 0.20 Bar.

In an exemplary embodiment of the invention, agitating comprises transmitting the agitation to a second segment of colon adjacent to the colon segment. Alternatively or additionally, agitating comprises rotating the mixture in the colon segment at a rate of 10-100 RPM. Alternatively or additionally, agitating comprises vibrating the mixture in the colon segment at a rate of 33-120 Hz. Alternatively or additionally, agitating comprises alternatingly inserting a volume of a pressurized fluid into the colon and a volume of a pressurized gas into the colon, the pressure of the gas being at least 0.2 ATM above the pressure of the liquid.

In an exemplary embodiment of the invention, inserting additional liquid comprises inserting the liquid at a range of between 400 cc/min and 2000 cc/min.

In an exemplary embodiment of the invention, the method further comprises shredding of pieces of fecal matter to an average size of less than 1 mm.

In an exemplary embodiment of the invention, the method further comprises controlling at least one of the filling, the agitating, the inserting and the emptying to clean the colon at a rate of at least 10 cm/second.

In an exemplary embodiment of the invention, the method further comprises controlling at least one of the filling, the agitating, the inserting and the emptying to clean the colon at an efficiency of at least 95%.

There is provided in accordance with an exemplary embodiment of the invention a controller programmed to dynamically control liquid input into a colon segment and material output from the colon segment so as to maintain a mixture of liquid and feces at least 60% full within the colon segment during changes in volume of the colon segment.

There is provided in accordance with an exemplary embodiment of the invention a device for cleaning a colon comprising:

a) a fluid input tube for supplying fluid to a colon segment being cleaned, the tube extending from outside the colon to the colon segment;
b) a material output tube through which liquid and fecal matter may be removed, the tube extending from outside the colon to the colon segment; and
c) an agitation element for transferring a sufficient amount of energy to at least one of dislodge fecal matter from at least 50% of the surface area of walls of the segment and break-down at least 50% of the volume of relatively large fecal matter blocks inside the segment. Optionally, the agitation element is a helix. Alternatively or additionally, the agitation element is a paddle.

There is provided in accordance with an exemplary embodiment of the invention a device for cleaning a colon comprising:
a) a material output tube through which liquid and fecal matter may be removed, the tube extending from outside the colon to the colon segment; and
b) a fluid flow pulsator which supplies alternating pulses of pressurized liquid alternating with pressurized gas, wherein a pressure of the gas is at least 0.2 atmospheres above a pressure of the liquid, and a rate of input of the liquid into the colon segment is at least 400 cc/min. Optionally, the pressure of the liquid is substantially equal to an ambient pressure of a liquid-fecal mixture inside the colon.

There is provided in accordance with an exemplary embodiment of the invention a device for cleaning a colon comprising:
a) a fluid input tube for supplying fluid to a colon segment being cleaned, the tube extending from outside the colon to the colon segment;
b) a material output tube through which liquid and fecal matter may be removed, the tube extending from outside the colon to the colon segment; and
c) a filter covering the output tube, the filter having a plurality of openings substantially parallel to a long axis of the device, wherein a dimension of the openings substantially perpendicular to the long axis is at least 3 mm.

There is provided in accordance with an exemplary embodiment of the invention a colon-cleaning device at least 60 cm in length and capable of cleaning a colon at a rate of 15 cm per minute comprising
a. A liquid input tube configured to deliver at least 0.7 liters per minute into the colon at a distal end of the input tube;
b. An output tube which encloses
 i. A mechanism for reducing matter chunks entering the input tube to sizes of less than 1.0 mm; and
 ii. A transport mechanism capable of removing material from the colon to outside the body at a rate of at least one liter per minute;
c. A controller programmed to control input flow and output flow so as to establish and maintain a condition in which a colon portion being cleaned is at least 60% filled with liquid.

There is provided in accordance with an exemplary embodiment of the invention a device for continuously cleaning a colon comprising:
a) a fluid input tube for supplying fluid to a colon segment being cleaned, the tube extending from outside the colon to the colon segment;
b) a material output tube through which liquid and fecal matter may be removed, the tube extending from outside the colon to the colon segment; and
c) a sensor configured to at least one of: determine relative amounts of liquid and of gas present near a tip of the cleaning device, measure input flow rates, measure output flow rates; and
d) a controller configured to fiddle with at least one of an input flow rate and an output flow rate to maintain a volume of a segment of the colon to be mostly full of the fluid and feces.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:
FIGS. 1A-1D are simplified schematics of a colon cleaning system;
FIGS. 2A-2J are simplified schematics of colon cleaning systems agitating liquids in a filled colon, according to some embodiments of the invention;
FIGS. 7A and 7C-7F are simplified schematics of systems for alternatingly pulsing two types of fluids through a conduit, according to some embodiments of the invention.

FIGS. 9A-9E are simplified schematics of a colon cleansing system utilizing sensors to control fluid input into the colon, according to some embodiments of the invention;

DESCRIPTION OF SPECIFIC EMBODIMENTS OF THE INVENTION

Figure 2A:
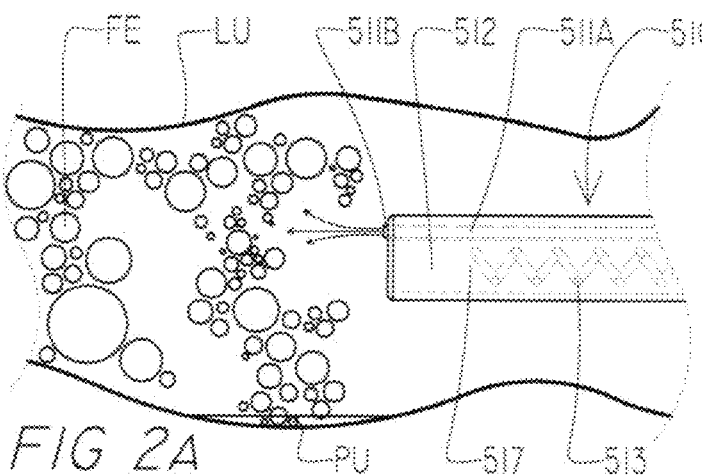

The present invention, in some embodiments thereof, relates to devices and methods for cleaning body cavities and, more particularly, but not exclusively, to devices and methods for cleaning a colon.

An exemplary embodiment of the invention comprises filling or partially filling a section of colon or other body lumen with a fluid and/or liquid optionally comprising of gas, and agitating the fluid. The agitation transfers a sufficient amount of energy to dislodge fecal matter from the intestinal walls and/or to dismantle relatively large fecal matter blocks into relatively smaller parts. The dislodged and partially dissolved fecal matter can then be removed from the intestine, cleaning the colon segment.

An exemplary embodiment of the invention, comprises mixing at least one liquid with at least one type of gas (e.g. air) in proportions of as much as 50% gas, 60% gas, 70% gas, 80% gas, or other smaller, intermediate or larger percentages, and agitating the liquid and/or gas to such an extent that the liquid and/or gas interact with matter in the intestine as if a single turbulent fluid.

In an exemplary embodiment of the invention, energy is transferred to liquid filling or partially filling a colon by use of an agitating device, such as a rotating device (helical device, turbine, paddle, other), optionally within a tube filled with liquid communicating with liquid outside the tube and/or by use of a plurality of liquid jets (e.g., water) angled to create rotational motion in surrounding liquid. For example, the liquid inside the colon is agitated by causing the liquid to rotate at about 10 RPM, about 20 RPM, about 60 RPM, about 100 RPM, or other smaller, intermediate or larger rates of rotation are used. For example, the liquid is agitated by applying energy in the form of vibration induced in the liquid, such as vibrations between 33-120 Hz, or other smaller, intermediate or larger ranges are used. For example, vibrations in the liquid substantially along a long axis or omni-directional vibrations are between 0.5-20 Hz, or 5-10 Hz, or other smaller, intermediate or larger ranges of vibration are used. In some embodiments, an amount of energy sufficient to agitate the fluid and/or feces in an omni-directional manner is applied.

In an exemplary embodiment of the invention, the liquid inside the colon is agitated (e.g., energy is transferred to the liquid) using pulsed sequences, wherein liquid segments alternating with gas segments within a fluid delivery tube, are inserted into the colon. Alternatively or additionally, liquid is mixed with gas. For example, fluids (e.g., water) and/or gas (e.g., room air) are inserted at a rate of about 400 cc/min, about 700 cc/min, about 1000 cc/min, about 1500 cc/min, about 2000 cc/min, or other smaller, intermediate or larger rates are used. In some embodiments, the flow rate of gas is relatively larger than the flow rate of liquid, for example, 700 cc of water cyclically alternating with 1000 cc of air. This arrangement may provide high speed pulsed liquid segments without requiring high input pressure, and/or also may provide omni-directional shock waves when used within a standing liquid.

In an exemplary embodiment of the invention, measurements of fluid input to the colon and/or measurement of fluid and solid output from the colon are compared to determine what quantity of fluid is present in the colon. Optionally, this information is used to maintain fluid input and/or output within safe proportions. For example, fluids and/or solids are removed from the colon at a rate of about 300 cc/min, about 1000/min, about 2000 cc/min, or other smaller, intermediate or larger rates are used.

In an exemplary embodiment of the invention, a sensor is used to determine relative amounts of liquid and of gas present near the inlet and/or outlet of the cleaning device. Optionally, data from the sensor is used to control fluid input and/or output to/from the device.

In an exemplary embodiment of the invention, a pressure inside the colon is maintained within a range, for example, 0-76 mbar, 5-50 mbar, 10-60 mbar, 25-60 mbar, 30-76 mbar, or other smaller, intermediate or larger ranges are used. Optionally, significant changes in the ambient pressure are detected and/or prevented, for example a decrease in pressure of up to 0.20 Bar or an increase in pressure of up to 0.06 Bar, or other smaller, intermediate or larger values are used. Optionally, the pressure rate and/or pressure change is maintained in the colon during cleaning, for example, during fluid input, fluid output and/or agitation of the fluid.

In some embodiments of the invention, a cross sectional profile of a cleaning device is reduced by having a flattened and/or crescent shaped lumen (e.g., evacuation lumen). Optionally, matter evacuation elements inside the lumen (e.g., rotating elements) are prevented from flailing and/or migrating by shoulder like indentations of the lumen wall.

In an exemplary embodiment of the invention, a filter prevents and/or reduces the risk of pieces of matter (e.g., feces) from blocking an outlet (e.g., tube used to remove feces) of the cleaning device. The openings in the filter have a dimension sufficiently smaller than the openings of the outlet of the cleaning device, for example, about 1 mm smaller, about 2 mm smaller, about 3 mm smaller, or other smaller, intermediate or larger sizes are used. The filter selectively admits fecal matter through, depending on size. Relatively large pieces of feces are prevented from entering and obstructing the outlet. Relatively smaller pieces of fecal matter can pass through, the pieces being sufficiently small not to obstruct the outlet. In an exemplary embodiment of the invention, the filter is comprised of bars and/or a mesh. In an exemplary embodiment of the invention, the filter comprises enough openings to maintain flow into the outlet during cleaning even if some of the openings become clogged with feces, for example, at least 2, at least 4, at least 6 openings, or other smaller, intermediate or larger number of openings are used. Optionally, the filter prevents and/or reduces contact between the colon wall and a rotating apparatus inside the outlet.

An aspect of some embodiments of the invention relates to controlling and/or adjusting colon cleaning parameters to achieve cleaning targets. In an exemplary embodiment of the invention, colon cleaning parameters are set and/or adjusted according to monitoring and/or feedback about the cleaning targets. Alternatively or additionally, cleaning parameters are based on a cleaning parameter table, such as having correlation data obtained by trial and error. One or more non-limiting examples of cleaning targets include: the rate of cleaning, the efficiency of cleaning. In some embodiments, one parameter is adjusted in order to affect a second parameter. One or more examples of indirect adjustment of parameters include; controlling the agitation of fluid and/or the proportion of fluid in the colon to control the cleaning rate and/or efficiency.

In an exemplary embodiment of the invention, methods and/or devices are provided for filling a section of colon with a fluid, to reach a fecal-fluid mixture that mostly fills a volume of the segment of the colon. The remainder of the volume in the segment of the colon (non fluid-fecal) is comprised of a gas, such as room air and/or $CO_2$. Non-limiting examples of the absolute volume of the colon segment include about 50 milliliters, about 150 mL, about 250 mL, about 500 mL, about 1 liter, about 2 liters, or other smaller, intermediate or larger volumes are used. Non-limiting examples of the absolute volume of the fecal-fluid mixture include about 50 milliliters, about 150 mL, about 250 mL, about 500 mL, about 1 liter, about 2 liters, or other smaller, intermediate or larger volumes are used. Non-limiting examples of the ratio of the fecal-fluid mixture to the volume of the segment include at least 50%, at least 60%, at least 70%, at least 80%, at least 90%, about 100% of the volume of the segment of the colon, or other smaller, or intermediate values are used.

In some embodiments, the section of colon is selected according to a length of the segment. For example, about 5 cm, about 10 cm, about 30 cm, about 50 cm, or other smaller, intermediate or larger lengths are used. Optionally, the segment of colon is manually selected by a user, such as by the physician, for example, the segment the physician is visually inspecting during a colonoscopy procedure. Alternatively or additionally, the segment of colon is related to the cleaning ability of the cleaning device, for example, the largest volume of the colon and/or the furthest distance that the cleaning device is able to clean from feces. Alternatively or additionally, the section of colon is related to the anatomy of the patient, for example, the tortuous nature of the colon naturally separates segments from one another.

In an exemplary embodiment of the invention, the segment is filled to be mostly full of the fluid-fecal matter mixtures, without mostly filling other segments and/or parts of the colon. For example, the filled segment is relatively lower than other nearby segments, and is filled by gravity. The patient can be moved and/or positioned to aid in placing the colon segment to be filled relatively lower than other nearby segments. Alternatively, other segments are also filled, for example, the entire colon or portions thereof are filled.

In some embodiments, the mixture mostly comprises of fecal matter, for example, if the colon is about 90% full of relatively dry fecal matter, the added fluid will mostly enter air spaces inside the feces, maintaining the fecal-fluid mixture ratio at about 90% of the volume of the segment of the colon.

In an exemplary embodiment of the invention, the volume of the colon segment is estimated and/or determined according to the dimensions of the colon during cleaning. The walls of the colon are relatively flexible and relatively elastic, allowing for a range of shapes and/or sizes. In some cases, the colon segment is mostly collapsed (e.g., if relatively empty) around any feces and/or liquid inside the segment. In such a case, the amount of the feces and/or fecal-fluid mixture is about 100% of the total volume of the colon segment. In some cases, the colon segment is partially and/or completely inflated (without stretching the walls), such as by filling the segment with $CO_2$ gas during a colonoscopy and/or the feces in the colon inflate the colon. In some cases, the colon segment is over-extended (e.g., an increase in diameter of the colon of over 100% as compared to the inflated state), such as by overfilling with gas and/or with fluid causing the colon walls to stretch. In an exemplary embodiment of the invention, the percent of the fecal-fluid mixture out of the total volume of the colon is dynamically determined according to changes in the dimensions of the colon.

In an exemplary embodiment of the invention, appropriate liquids include water or other liquids and may comprise supplemental additives such as drugs, osmotic solution, PEG based solution, or any other mixture of agents used in the medical field. Optionally, the supplemental additives aid in cleaning the colon, non-limiting examples include detergents, foam formers and/or wetting agents.

In an exemplary embodiment of the invention, the fluid-fecal mixture is agitated; energy is applied to the fecal-fluid mixture, such as by rotating, swirling, vibration, shaking, pressure waves and/or other types of motion imparted to the mixture of fluid-feces filling or partially filling the intestine. Optionally, energy is transmitted to the mixture through a non-fecal liquid (e.g., water), such as located between the device and feces. A non-limiting hypothesis is that the amount of energy transferred to the mixture is sufficient to cause an agitation of the mixture, wherein the fecal matter becomes detached from the intestinal walls and/or generally causes larger chunks of matter to break down into smaller elements. The fecal matter is then easily removed from the intestine using a suction device or any other device for transporting fecal matter out of the body.

In an exemplary embodiment of the invention, the energy transmitted to the mixture causes agitation of the mixture relatively in front of the cleaning device (e.g., the device inlet and/or outlet), for example, at least 2 cm distally, at least 5 cm, at least 10 cm, at least 15 cm, at least 20 cm, at least 30 cm, at least 50 cm, or other smaller, intermediate or larger values are used. Alternatively or additionally, the mixture relatively behind the cleaning inlet and/or outlet is agitated. Alternatively or additionally, the mixture surrounding the cleaning device is agitated. Optionally, the agitated mixture is removed. In some embodiments, fecal matter surrounding at least a part of the circumference and/or surface area of the colon segment is agitated, even if the colon is not full of feces, for example at least 20% of the circumference and/or surface area, at least 50%, at least 80%, about 100%, or other smaller or intermediate percentages are used. In some embodiments, fecal matter inside the volume of the colon segment is agitated (e.g., broken down into relatively smaller pieces), for example, at least 50% of the volume at least 80% of the volume, about 100% of the volume, or smaller, intermediate or larger percentages are used. For example, the agitation is sufficiently strong, to cause rotational motion of the mixture, thereby cleaning the entire circumference. Alternatively, a section of the circumference is cleaned.

In an exemplary embodiment of the invention, agitation is transmitted to the mixture from inside the cleaning device, for example by a rotational device inside the cleaning device, transmitting energy to a fluid inside the cleaning device, the fluid hydraulically transmitting the energy to feces. Alternatively or additionally, agitation is transmitted to the mixture directly, for example, by a rotational device outside the cleaning device, for example, transmitting energy directly to the feces.

In an exemplary embodiment of the invention, one or more non-limiting examples of devices used to cause agitation include; the rotational devices such as a screw and/or spring, a paddle, a brush, an element that vibrates, pointed fluid outlet jets, alternating pulses of pressurized fluid and pressurized gas. Two or more devices may be used sequentially and/or in combination, for example, a rotating screw may be used to achieve agitation inside the outlet of the device and alternating pulses may be used to achieve agitation near the inlet of the device (e.g., source of fluid provided by device into colon segment).

In an exemplary embodiment of the invention, flow and/or motion of the fluid-fecal mixture due to agitation is directed towards the device, such as to suck the mixture into the device outlet. Alternatively or additionally, flow and/or motion of the mixture due to agitation is directed not towards the device, for example, as random motion and/or motion away from the device inlet, such as to remove feces from the colon wall and/or to break down the feces. Non-limiting examples of motion include a relatively violent spinning rotational motion, a gentle flow into the cleaning device, forward/backward vibrational motion and/or motion caused by explosive-like forces.

In an exemplary embodiment of the invention, systems maintain a predetermined level of fluid fill (i.e. filling a segment of colon with liquid to a predetermined level or percentage of a fluid-fecal mixture inside the volume of the colon segment), for example, about 20%-100% full, about 60%-100% full, about 60%-90% full, about 80-95% full, or other smaller, intermediate or larger ranges are used. Optionally, the GI physician/operator will determine what degree of fill and what pressures are appropriate for a given patient. In many cases filling the colon nearly full of water will be most effective, but on some cases merely filling the segment to at least 20%, at least 30%, at least 40%, or other smaller, intermediate or larger filling values, and/or covering the outlet (e.g., outlet tube for feces and/or fluid) of the apparatus with water could be quite effective.

In an exemplary embodiment of the invention, the degree of fill is maintained during dynamic changes in the dimensions of the colon (e.g., using a controller). For example, if the physician selects the volume of the segment to be maintained at least at 90%, additional liquid will be inserted to keep the volume at least at 90% if the cross sectional size of the colon increases such as by the addition of $CO_2$ gas, or by the addition of the liquid itself. Alternatively, the cross sectional area of the colon may decrease, such as during removal of feces, in which case to maintain the 90% volume excess liquid can be removed. In an exemplary embodiment of the invention, the pressure is controlled at the same time as the degree of fill, for example, to prevent and/or reduce adverse events such as over-expanding the colon and/or sucking the colon wall tissue into the outlet tip of the device.

In an exemplary embodiment of the invention, the degree of fill is maintained while the device is working and/or cleaning. Optionally, the degree of fill is maintained during the fluid exchange inside the colon segment (e.g., inserting and/or removing fluid). Alternatively or additionally, the degree of fill is maintained during the agitation of the fluid. Alternatively or additionally, the degree of fill is maintained while maintaining pressure within the range.

OVERVIEW AND POTENTIAL ADVANTAGES

Colonoscopies (viewing the inside of the colon using an endoscopic device with the ability to perform medical procedures therein) are performed for a variety of clinical indications. Some of the most common include screening colonoscopies such as to search for early stages of colon cancer, and emergency colonoscopies, such as to search for a source of a lower gastrointestinal bleed.

In the case of a screening colonoscopy (e.g., performed every 5-10 years), a patient's colon is cleansed by having the patient drink relatively large volumes of a liquid that stimulates massive bowel movements. The procedure is generally unpleasant for patients and can take a relatively long time to complete. Furthermore, the patient's colon may not be entirely cleaned of feces, disturbing the ability of the physician to scan the internal bowel wall for cancer and to remove polyps.

The application describes herein an apparatus and a method for the cleaning of a colon. Some non-limiting potential advantages (embodiments do not need to meet some or even all of the potential advantages) include; relatively reduced procedure times (e.g., relatively reduced cleaning times), relatively improved procedure safety, ability to clean an unprepared or partially prepared colon, and/or ability to clean during a colonoscopy. For example, in the case of emergency colonoscopies, the time to prepare the patient may be very limited. A colon relatively full of feces causes difficulty for the physician to operate, such as to visualize and stop a source of bleeding.

For purposes of better understanding some embodiments of the present invention, as illustrated beginning with FIG. 2A of the drawings, reference is first made to the construction and operation of an intestinal cleaning device as illustrated by FIGS. 1A-1D.

FIG. 1A shows a section of colon with colon wall marked "LU", and within that colon section a standard colonoscope 500. Colonoscope 500 comprises a camera 504, a fluid input conduit (not shown) terminating in nozzles 501, a working channel 502 typically used to remove fluids and solid matter out of the body using suction or alternatively used to insert surgical tools into the colon, and a steering segment 503 adjustable by manipulating knobs on a proximal portion of the colonoscope, which knobs enable a user to steer the colonoscope's tip within the colon. When colonoscope 500 is used in complementary colon cleaning, water under pressure is provided in the fluid input conduit and caused to issue from nozzles 501 as pressurized jets of water. When the physician or other operator observes a portion of fecal matter (marked FE1 and FE2 in the drawing) adhering to the intestinal wall, he turns the proximal knobs to bend steering section 503 in a way that aims the colonoscope tip towards that matter. He then provides a jet of water from nozzles 501 towards the observed fecal matter, thereby dislodging it from the intestinal wall. As shown in FIG. 1B, the dislodged fecal matter mixed with water from nozzles 501 then typically drains downward under the influence of gravity and pools in small puddles comprising water and fecal matter. Such a pool or puddle is marked "PU" in FIG. 1C.

In an example of a cleaning procedure, the GI physician individually aims the tip of the colonoscope at the various feces deposits, washing them individually off the intestinal wall, then stops the water jet, aims the distal end of colonoscope 500 towards the pooled water and dislodged fecal matter (PU), and uses suction provided in output conduit 502 to suck up and remove the pooled water and feces. This process is shown in FIG. 1D. Typically, the sequence of steering, cleaning with water jet, re-steering towards the pooled matter, and suction, practiced repeatedly, in a cyclical manner, each time handling a small concentration of fecal matter individually identified and aimed at and cleaned, until eventually the entire colon wall is clean.

As mentioned in the background section above, an example of a cleaning device is provided by PCT application WO\2009\143201 by Gordon. This device is also known in commerce as "Easy-Glide", and differs from the above description in that the "Easy-Glide" device is external to the endoscope, provides an input water conduit and output feces-transporting conduit, and therefore leaves the colonoscope's working channel free for other uses. Use of the "Easy-Glide" device, however, is similar to the procedure described above: the GI physician has to steer the colonoscope tip towards each concentration of fecal matter and again towards the pooled fecal matter after this has been washed off the intestine wall by a water jet, and the process must be repeated over and over in order to obtain a clean colon wall.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways. In particular, although descriptions of embodiments presented below refer to the colon and to cleaning of the colon, it is to be understood that the invention is not limited to that context and can be used for cleaning other body lumens, for example, the upper gastrointestinal track and/or stomach. It is further noted that embodiments presented below as features of an endoscope or colonoscope can also be practice in a stand-alone system sans endoscope, or in an add-on system attached to an endoscope and/or used together with an endoscope, and conversely that embodiments presented in stand-alone or add-on format can also be incorporated in an endoscope or colonoscope.

In an exemplary embodiment of the invention, the cleaning device is designed to clean feces from the colon. Non-limiting examples of 'cleaning feces' include; cleaning a relatively large amount of feces (for example, at least 500 cc, at least 1000 cc, at least 2000 cc, or other smaller, intermediate or larger volumes of feces), cleaning relatively dry, relatively hard and/or relatively large feces (e.g., feces requiring the addition of sufficiency fluid and/or energy imparted to the feces to break apart and/or move the feces).

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Clinical Scenarios

In an exemplary embodiment of the invention, the cleaning device can be used to clean colons in a variety of clinical scenarios. Optionally, at least some of the cleaning parameters (e.g., input/output fluid rates, liquid rotation rate, cleaning rate, cleaning efficiency, working pressure) are selected according to the clinical scenario, for example, according to a table of correlation values, for example, as described with reference to the section "Exemplary Control System". Alternatively or additionally at least some of the cleaning parameters are not dependent on the clinical scenario.

In an exemplary embodiment of the invention, the cleaning device is used as an add-on to an endoscope (e.g., colonoscope), for example, to clean before and/or during a procedure. Alternatively or additionally, the cleaning device is used alone, for example, to clean the colon if a procedure is not being performed.

One or more non-limiting examples of clinical scenarios include:

An 'unprepared' colon, for example, of a patient requiring an emergency colonoscopy.

An 'overfilled colon', for example, of a patient with chronic constipation (e.g., cancer patient with abdominal metastases) requiring occasional cleaning. In some embodiments of the invention, cleaning is performed alone, such as unrelated to a colonoscopy procedure.

Cleaning for 'well being', for example, as a preventive measure in certain patient populations, such as frail elderly patients living alone.

A 'semi prepared' colon, wherein the partial preparation was intended, for example, to perform a colonoscopy in a patient that would be unable to tolerate a full cleaning preparation, such as the elderly.

A 'semi prepared' colon, wherein the partial preparation was unintentional, for example, a patient that did not understand how to follow the preparation instructions.

Some potential advantages of using the apparatus and/or method as describe herein, such as during one or more of the scenarios described include; relatively reduced procedure times, relatively improved procedure safety, ability to clean an unprepared or partially prepared colon, and/or ability to clean during a colonoscopy.

Filling the Colon with Liquid, Swirling the Liquid

Attention is now drawn to FIG. 2A and the following figures, which present various exemplary embodiments. Some embodiments are distinguished in that they are designed to be applied in a colon or other conduit which is largely or completely filled with fluid, typically a mixture of water, air, and dislodged fecal matter. In some embodiments the method comprises practicing a cleaning function in a colon substantially full of fluid in which water or other liquids predominate and represent more than 30% by volume, and in some cases more than 60% by volume. Using these devices and methods, superior cleansing results can be obtained, and the process is relatively faster and more efficient because there is typically little or no need to steer the endoscope tip specifically toward individual deposits of fecal matter. In some embodiments, water-jet cleaning and exhaust suction can be practiced simultaneously.

It is to be noted that in the following, various features and embodiments are presented in isolation for simplicity of exposition, but it is to be understood that embodiments presented herein can be used in a variety of combinations, and that the present disclosure should be understood to include all such combinations of embodiments and/or features.

Referring again to the drawings, FIGS. 2A-2J present embodiments of methods and devices for cleaning a body lumen and/or conduit, for example, a colon, such as a segment of the colon (e.g., ascending, descending, transverse portions or partial segments thereof), referred to in the following as colon cleaner 510A.

FIG. 2A shows a portion of a colon (marked "LU") into which cleaner 510A has been introduced. Cleaner 510A comprises at least one fluid input conduit 511A optionally terminating in a nozzle 511B. Cleaner 510A also comprises an output conduit 512 used to evacuate fluids & fecal matter from the body. Conduit 512 houses a rotating apparatus 517, such as helical apparatus 513 shown in the figure. Rotating apparatus 517 may be powered by an external motor connected at its proximal end (not shown in the figure). Helical apparatus 513 is designed to rotate on its axis within conduit 512, and serves to transport fluid and fecal matter through conduit 512 and out from the body. Optionally, helical apparatus 513 may be implemented in the form of threads of a screw rather than a helical 'spring' format, or as a helically formed spiral brush, or as one helical spring turning freely within a second helical spring, or in any other format which will impart motion in a proximal direction (i.e. out of the body) to fluids and fecal matter within conduit 512. Optionally, conduit 512 may also be used to inject fluid into the colon or other body lumen being cleaned, the process of injecting fluid and the process of evacuating fluid alternating with one another in a cyclical manner.

Figure 2B:
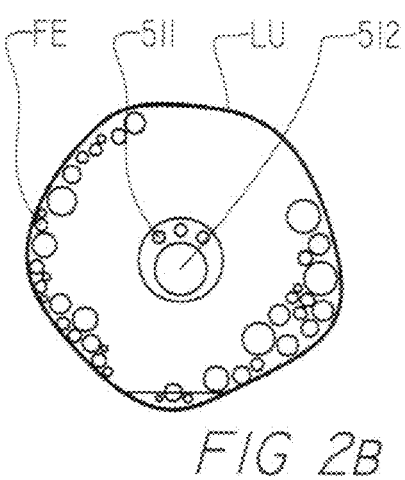
Figure 2C:
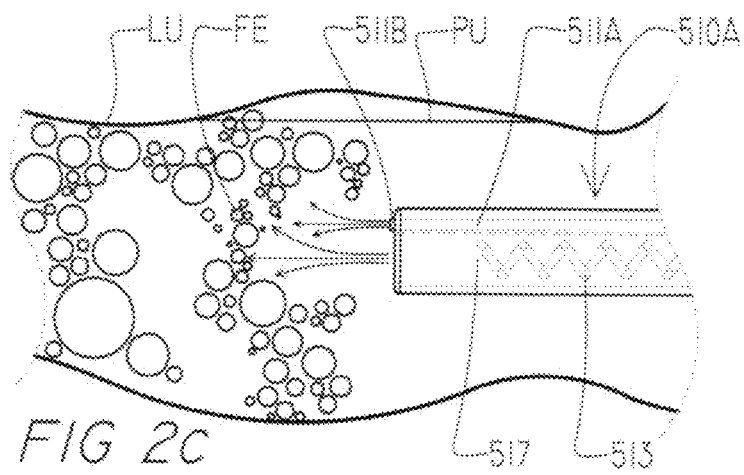
Figure 2D:
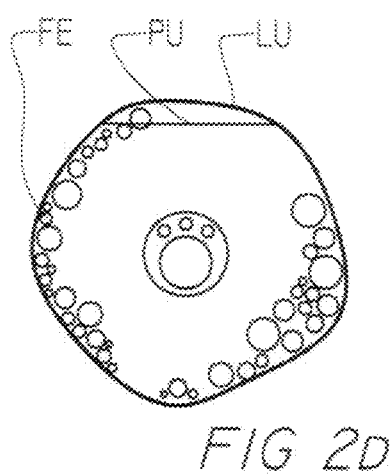

FIGS. 2A-2F illustrates a process. FIGS. 2A and 2B represent a "before" picture wherein fecal matter (FE) covers the colon wall (LU). The GI physician can use cleaner 510A without needing to steer it towards fecal concentrations. Optionally, the inlet and/or outlet of cleaner 510A are placed at non-specific locations within the colon segment. Optionally, cleaner 510A is steered (e.g., moved by a physician) within the colon segment to the non-specific location, for example, to relatively improve cleaning performance. The non-specific location can achieve the required colon cleaning effect, such as by allowing sufficient agitation to be provided to the liquid in the colon as described herein, for example, by allowing omni-directional agitation. Placing cleaner 510 at certain positions can relatively increase the cleaning performance, for example, cleaner 510A may be left to "float" in the colon lumen without any pre-set direction. A potential advantage of cleaning by placing and/or steering cleaner 510A to the non-specific location is relatively improved and/or easier colon cleaning procedures. For example, the physician does not need to steer the cleaner to individual fecal deposit, a relatively time consuming procedure. FIGS. 2C and 2D show fluid, primarily a liquid such as water or water mixed with other substances, being introduced through conduit 511A/B and optionally also through conduit 512. (Note: in some embodiments, conduit 511A/B may be absent, conduit 512 serving both as input conduit and as output conduit.)

Figure 2E:
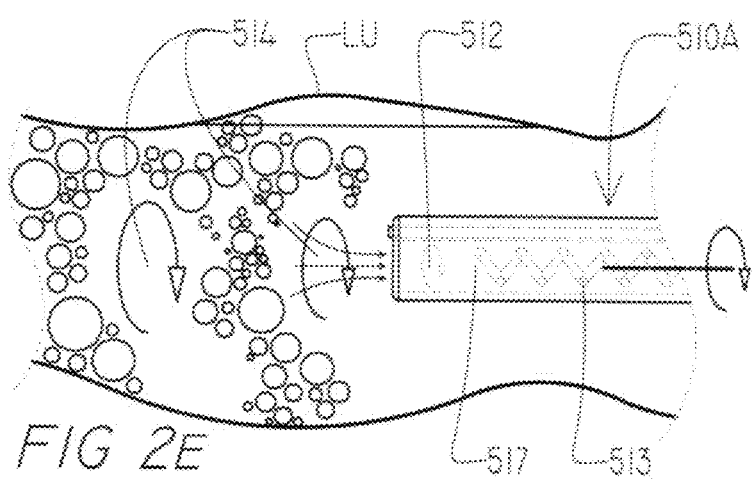
Figure 2F:
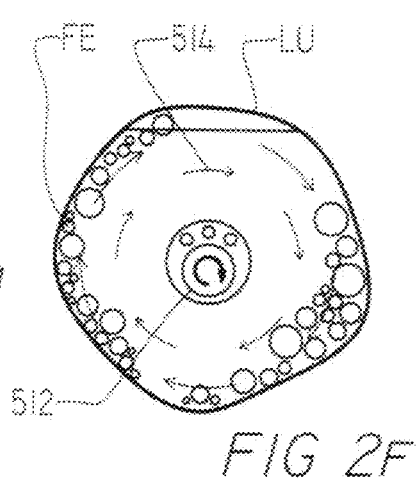

The label PU marks the 'water level' to which the colon is being filled in the exemplary embodiment shown in these figures. When the colon is filled to the PU level, or optionally while filling of the colon is still taking place, the physician operator may turn on the external motor (not shown) which powers rotation of helical apparatus 513. This situation is shown in FIGS. 2E-2F.

Rotation of helical apparatus 513, which may be a helix in 'coiled-spring' form, or a screw-thread configuration, or any similar structure may produce fluid flow in a proximal direction in conduit 512. The fluid flow may result in evacuation of fluid and fecal matter through conduit 512 and out of the body. In some embodiments element 513 is formed as a helix. Rotating the helix in an appropriate direction can move fluid and solids along conduit 512 in a direction which carries them out of the body. Optionally, use of a helix in this context also contributes by shredding pieces of fecal matter which might otherwise block conduit 512. Element 513 therefore can serve to keep conduit 512 open at all times. Element 513 can provide a safety feature preventing over-pressuring the colon, which could otherwise present a surgical risk.

In addition, helical apparatus 513 or any other rotating apparatus 517 (for example, paddles presented in FIGS. 2G-2J and turbines presented in FIGS. 6A-6C, both discussed below) can produce the following two effects:

(a) Inducing generalized movement in fluids outside conduit 512, which can produce an enhanced cleansing effect. Rotation of rotating apparatus 517 within evacuation conduit 512 can generate a rotational movement of fluids within conduit 512. In some embodiments, these fluids are continuous with fluids outside conduit 512 and within the colon lumen. Rotation of fluids within conduit 512 can induce rotation of the fluids within filled segment 514 of the colon lumen. Such induced rotation of fluids within the body lumen is referred to herein as a "projection effect".

In an exemplary embodiment of the invention, the rate of rotation of fluid within filled segment 514 is substantially less than the rate of rotation of rotating apparatus 517, such as due to frictional forces. For example, apparatus 517 rotates at about 2000-7000 RPM translates into about 10-400 RPM rotation of liquid in filled segment 514.

(b) Vibration: rotation of rotating apparatus 517 within conduit 512 may generate vibration. In some embodiments rotating apparatus 517 may be weighted asymmetrically, (e.g. a weight may be added asymmetrically to one side of a helix, so as to enhance generation of such vibrations). When cleaner 510A is used in a liquid-filled colon as taught above, vibrations generated by rotating apparatus 517 can transmitted very efficiently to the surrounding liquid. Such vibration can be effective in breaking down clumps of fecal matter into small parts, and/or having the effect of helping to "peel" fecal matter from the colon wall.

In some embodiments, the vibrations are transmitted to one or more adjacent segments of the colon through the colon wall and connecting tissues, for example, in a tortuous colon. The transmitted vibrations can dislodge and/or break down feces in the adjacent segments, potentially resulting in relatively improved cleaning times and/or cleaning efficiency.

In an exemplary embodiment of the invention, vibrations occur in at least one plane. Optionally, vibrations occur substantially along the longitudinal axis, for example 'front' and 'back' vibrations. Alternatively or additionally, vibrations are omni-directional. Longitudinal vibrations may occur as a result of mismatches of movement between rotating apparatus 517 and conduit 512 (e.g., due to differences in lengths and/or diameters). In some embodiments, vibrations occur intentionally (e.g., by a controller and/or user). Alternatively or additionally, vibrations that occur unintentionally such as by movement of the motor and/or during use of the cleaning device are used in combination with controlled vibrations to achieve a desired set of vibrations.

In an exemplary embodiment of the invention, agitation such as vibration of the fluid inside the colon segment is created using at least one element and/or using a combination of elements, non-limiting examples of elements include; the fluid inlet, the fluid outlet, and/or a separate tube, each of the elements optionally comprises an agitation element (e.g., the rotating spring) to agitate and/or vibrate the fluid.

The effects listed above which can result from rotation of helical apparatus 513 and/or any other rotational apparatus 517 within conduit 512, (evacuation of materials, induced rotation of liquids, and transmitted vibration), individually and in combination can produce a cleansing effect within the colon or other body lumen.

In some embodiments, additional elements and/or alternative elements may be added to, or substituted for, helical element 513, for example to agitate fluids within the colon and outside conduit 512. FIGS. 2G and 2H show a rotational element 517 which is a flat paddle 515 within conduit 512 at the distal end of a connecting flexible rod or shaft 516, with shaft 516 connected either to a helical apparatus 513 or directly to a proximal motor operable to rotate paddle 515. FIGS. 2I and 2J, where paddle 515 is embodied as a multi-bladed paddle. An exemplary embodiment of a multi-bladed paddle is shown, with four blades provided in an 'X' format, the blades marked 515A and 515B on the Figure.

Figure 6A:
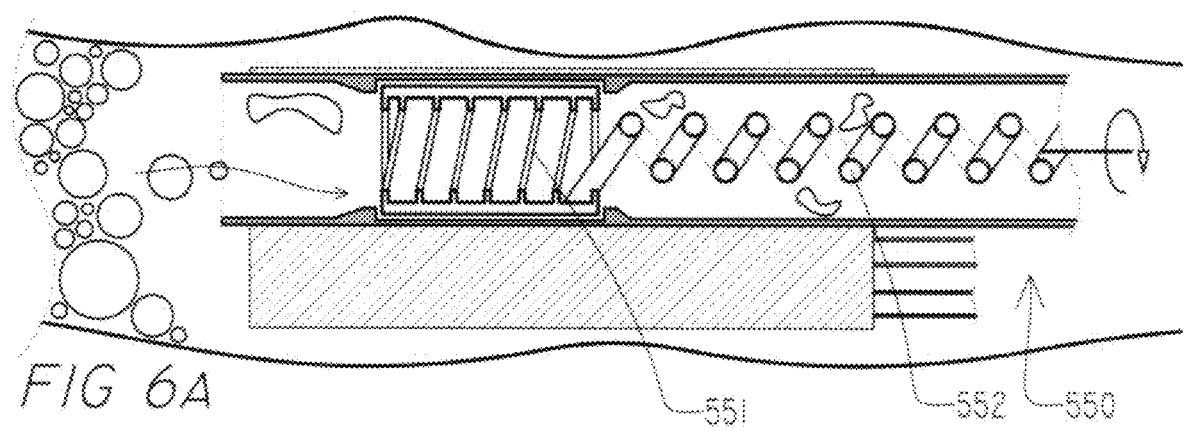
FIGS. 6A-6C are simplified schematics of a colon cleaning system comprising turbines within an evacuation conduit, according to some embodiments of the invention.
Figure 6B:
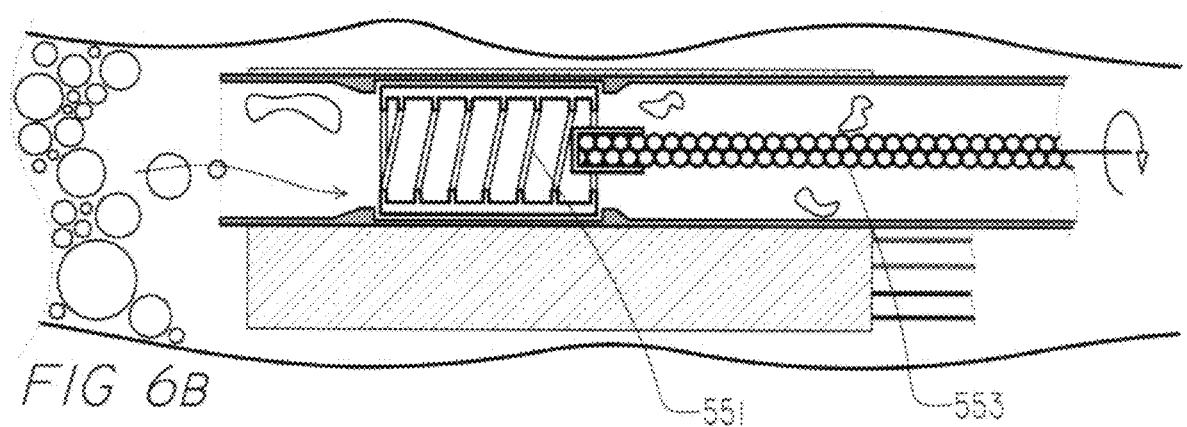
Figure 6C:
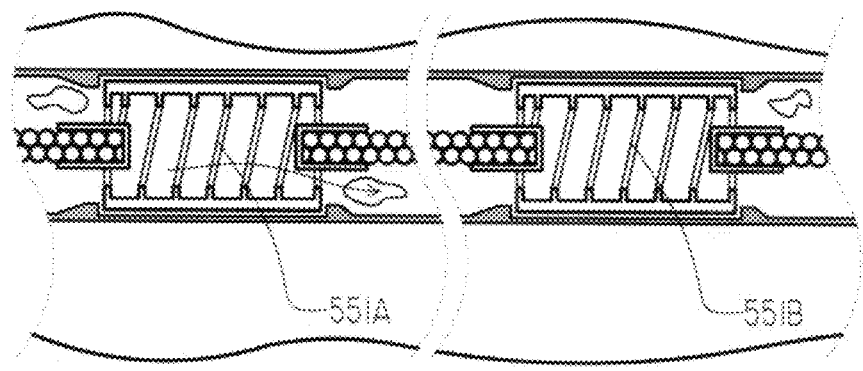

It is to be noted that paddles 515 are exemplary implementations, and not limiting. Any form of paddle (including irregular shaped paddles, paddles with holes, a rotary array of fins) may be used, and non-paddle element may be used. In some embodiments, a turbine arrangement (fins turning within an enclosure) may be used, as shown in FIGS. 6A-6C. In general, element 517 is any element which imparts a rotary motion to fluid within conduit 512, that motion being of sufficient strength to propagate outside of conduit 512 and impart rotary or turbulent motion to fluids outside conduit 512, such that those movements propagate within the colon and serve to loosen and detach fecal matter from the colon walls.

In some embodiments elements 513 and 515 are contained within conduit 512. This can prevent the colon wall from direct contact with these rotating elements, which might otherwise damage the wall.

In an exemplary embodiment of the invention, a colon section is filled or partially filled with liquid, then motion is induced in the liquid and the section is cleaned and evacuated by suction. Optionally, filling, motion inducing, and cleaning and evacuation are practiced simultaneously in a continuous process, while the cleaning device is (optionally) advanced the length of the colon. Required liquid levels in a colon section being cleaned can be maintained by operator control or can be maintained automatically as explained below.

Method of Cleaning the Colon

Figure 11:
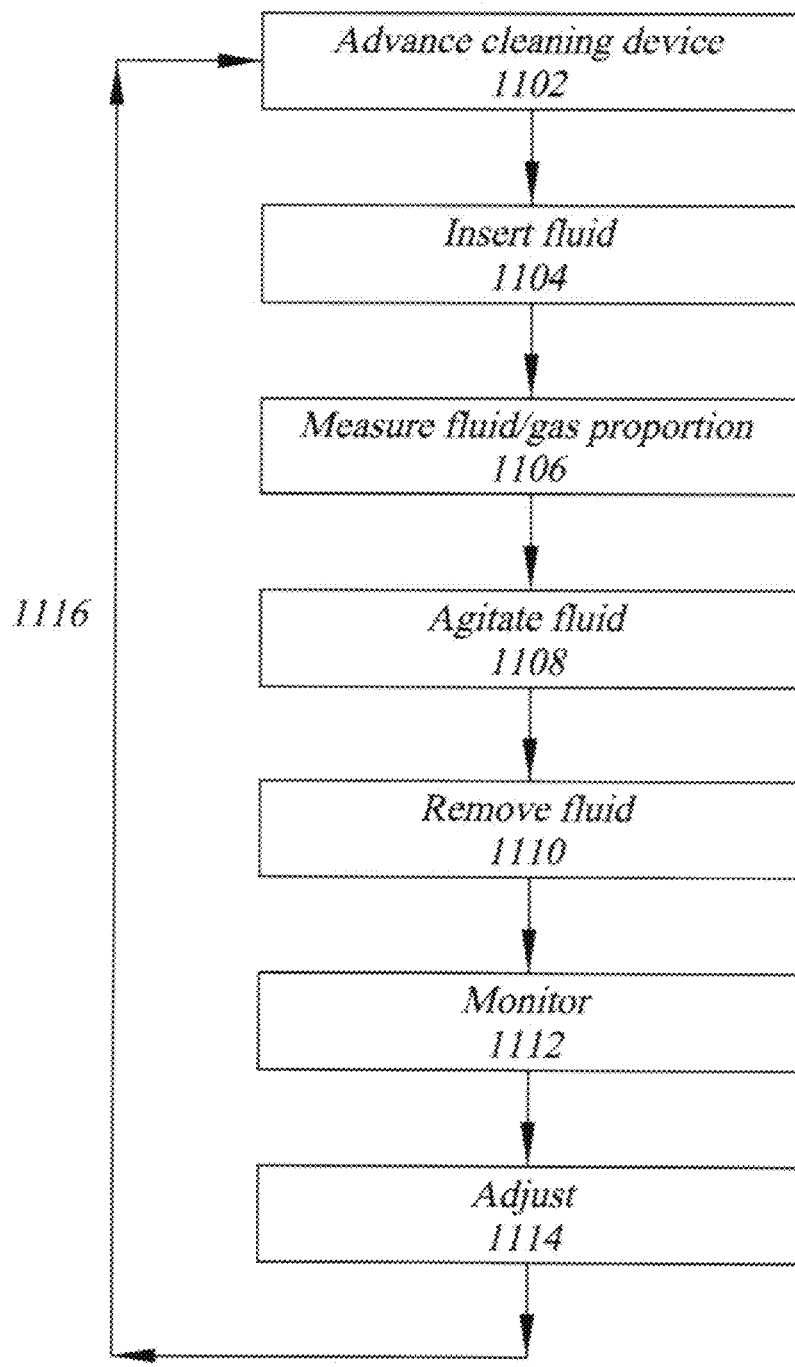
FIG. 11 is a flowchart of a method of cleaning the colon, in accordance with an exemplary embodiment of the invention.

FIG. 11 is a flowchart of a method of cleaning the colon, in accordance with an exemplary embodiment of the invention. In an exemplary embodiment of the invention, at least some of the method of cleaning is under automatic control, for example by controller 1002 as described with reference to the section "Exemplary Control System". Alternatively or additionally, at least some of the method is under manual control, such as by the physician performing the procedure.

Optionally, at 1102, a colon cleaner (e.g., cleaner 510A) is advanced inside the colon, for example, as illustrated with reference to FIG. 2A, in accordance with an exemplary embodiment of the invention. Alternatively, the colon cleaner is introduced inside the colon but kept at a constant position. Non-limiting examples of advancing the colon cleaner include advancing an endoscope having the device coupled thereto, advancing the device independently (e.g., manually such as by a physician pushing device, automatically such as by device self propelling and/or 'walking'), advancing the device over a guidewire.

At 1104, fluid is introduced into the colon, in accordance with an exemplary embodiment of the invention. For example, as described in the section "Filling the colon with liquid, swirling the liquid".

Optionally, at 1106, the proportion of fluid in the colon (e.g., colon segment) is measured and/or estimated, in accordance with an exemplary embodiment of the invention. For example, as described with reference to the section "Systems for maintaining colon fill levels: Measuring water levels". In an exemplary embodiment of the invention, the submergence of the colon cleaner in the fluid is detected.

At 1108, the fluid (e.g., introduced liquid and feces) inside the colon (e.g., colon segment) is agitated such as by vibration, water jets, rotational motion and/or shock waves, in accordance with an exemplary embodiment of the invention. For example, as described with reference to the sections "Filling the colon with liquid, swirling the liquid", "Swirling liquid motion produced by circularly directed water jets" and/or "Pulsing systems".

At 1110, fluid and/or waste is removed from the colon, in accordance with an exemplary embodiment of the invention. For example, as described with reference to the sections "Filling the colon with liquid, swirling the liquid", "Cleaning systems with turbines" and/or "Backward-pointing water jet". Optionally, the waste is shredded during removal.

Optionally, at 1112, the process is monitored, for example, the pressure inside the colon is measured and/or estimated (e.g., by a sensor), in accordance with an exemplary embodiment of the invention. For example, monitoring occurs as described with reference to the sections "Systems for maintaining colon fill levels: Measuring input/output" and/or "Systems for maintaining colon fill levels: Measure water levels".

Optionally, at 1114, adjustments are made to the process, in accordance with an exemplary embodiment of the invention. For example, based on monitoring as in 1112 and/or based on the proportion of fluid as in 1106, the input and/or output fluid rates can be suitably adjusted up or down to achieve targets such as the proportion of fluid in the colon as in 1106 and/or to control the pressure inside the colon.

Optionally, at 1116, the process is repeated, with optional adjustments as determined in 1114.

In some embodiments of the invention, at least some of the process occurs substantially in parallel, for example, at least some of advancement as in 1102, fluid insertion as in 1104, fluid agitation as in 1108 and/or fluid removal as in 1110. Alternatively, at least some of the process occurs in a step-wise manner. Optionally, measuring as in 1106, monitoring as in 1112 and/or adjustments as in 1114 occur substantially in parallel and/or during specified times and/or after specified actions.

Cleaning Module Attachment to Colonoscope

Figure 3A:
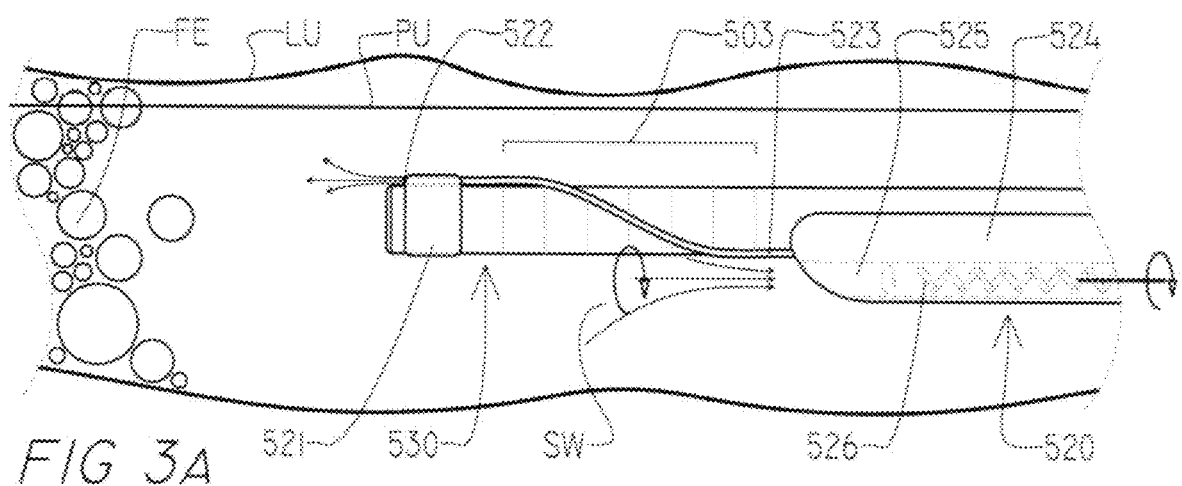
FIGS. 3A-3C are simplified schematics of colon cleaning systems attachable to a colonoscope, according to some embodiments of the invention.
Figure 3B:
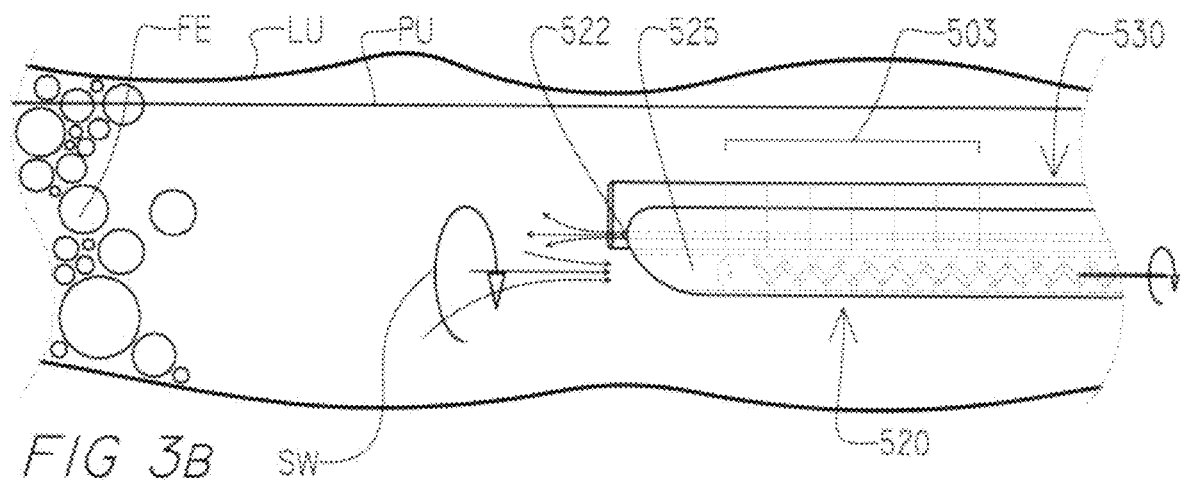
Figure 3C:
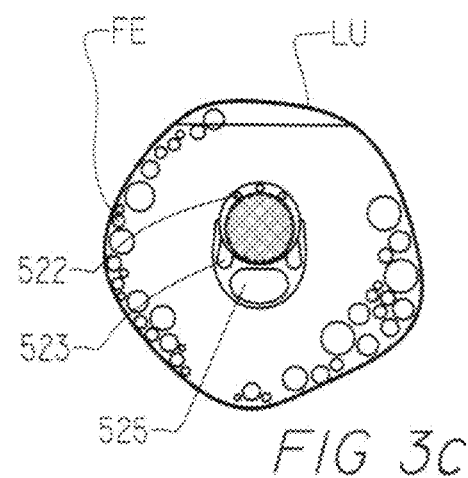

Attention is now drawn to FIGS. 3A and 3B, which show embodiments wherein an independent cleaning module 520, substantially as described above, is presented for use with (and optionally connected to) an endoscope or colonoscope 530, which can be a standard colonoscope. Optionally, cleaning module 520 is an external add-on attachment to colonoscope 530. In FIG. 3A the main body of cleaner 520 is positioned somewhat proximally to a distal end of endoscope 530, and a fluid input conduit 522, is advanced to a distal end of colonoscope 530, where it is attached by attachment band 521. An advantage of the construction shown in FIG. 3A is that cleaning device 520, which is likely to be somewhat stiff in construction because of the rotating mechanical devices it contains, is positioned proximally with respect to the steering mechanism 503 of endoscope 530, which is therefore able to be steered and directed freely without the steering process being influenced by the presence of cleaner 520. In an alternative construction shown in FIG. 3B, distal ends of cleaning device 520 and colonoscope 530 are positioned substantially side by side. In both cases, cleaning device 520 provides cleaning services, potentially leaving the working channel of colonoscope 530 available for other surgical work. Round arrows labeled 'SW' and arrows pointing into outlet conduit 525 illustrate swirling and/or agitation motion in the liquid in the colon, for example, induced by a rotation element 526.

In some embodiments, a cleaning module (e.g., one or more of the embodiments described herein, and/or any subcombinations thereof) is designed to be entirely and/or partially inserted into a working channel of a colonoscope (e.g., colonoscope 530), for example, by designing relatively smaller components to fit inside the working channel. Non-limiting examples of the size of the working channel into which the components can fit include; less than 2 mm in diameter, less than 3.5 mm in diameter, less than 5 mm in diameter, or other smaller, intermediate or larger values are used. Optionally, all of the elements comprising the cleaning device (e.g., as described herein) are inserted into the working channel of the colonoscope. Alternatively, some of the elements are inserted inside the working channel, and some of the elements are external. One or more non-limiting examples of elements include; fluid supply pipe, fluid removal pipe, rotational element, grinding element, fluid/gas pulsating system, and/or filter.

In an exemplary embodiment of the invention, the cleaning module 520, optionally connected to the endoscope or colonoscope is insertable relatively far into the colon (e.g., from the anal sphincter), for example, at least 40 cm, at least 60 cm, at least 100 cm, at least 150 cm, at least 200 cm, or other smaller, intermediate or larger distances.

Exemplary Embodiments for Graining and/or Exhausting Fecal Matter

Attention is now drawn to FIGS. 12A-12F, which present some embodiment of the invention which include features that facilitate 'graining' of fecal matter within an evacuation conduit of a cleaning device. Optionally, 'graining' is created by turbulence within the conduit and/or by grinding and/or cutting the pieces and/or by pulling the pieces apart by subjecting the pieces to contradictory pulling forces.

FIGS. 12A-12F present some embodiments of cleaning devices having a multi-lobe exhaust lumen, in accordance with some embodiments of the invention. The lumen comprises a plurality of co-aligned lobes running side by side along at least a portion of the length of the lumen.

Figure 12A:
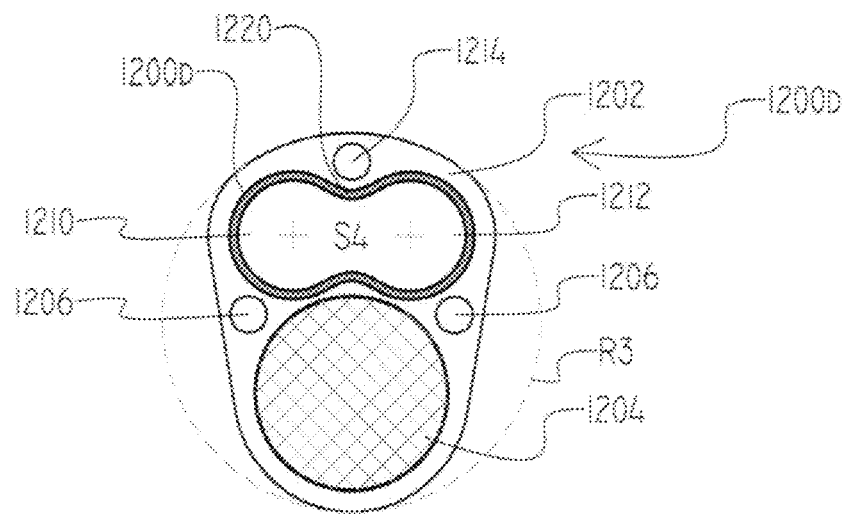
FIGS. 12A-12F present cleaning devices each having a multi-lobe exhaust lumen which comprises a plurality of co-aligned (substantially parallel) lobes running the length of the lumen, according to some embodiments of the invention.

FIG. 12A shows a device 1200D comprising within a housing 1202 an (optional) endoscope optic 1204, one or more fluid input conduits 1206, and a matter exhaust lumen 1208 shaped within housing 1202 and which comprises a first lobe 1210 and a second lobe 1212. Lobes 1210 and 1212 are in fluid communication along at least a part of their length, which is to say that fluid and other matter can flow between them. Each lobe has a central axis (shown as a "+" in the figure) and optionally has a cross-section at least part of which has a circular border, as shown in FIG. 12A. Lumen 1208 as a whole has a roughly "figure 8" shape, optionally providing room for a fluid input lumen 1214 as shown in FIG. 12A.

Figure 12B:
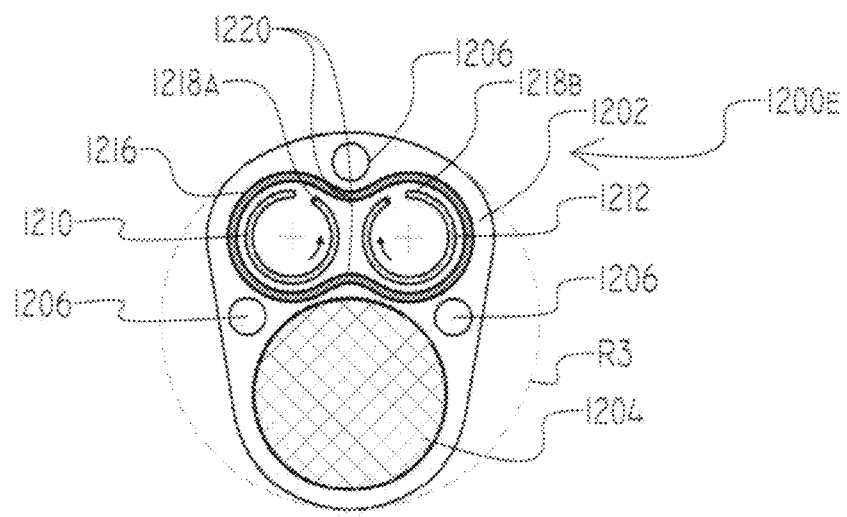

FIG. 12B shows a cleaning device 1200E wherein a two-lobed exhaust lumen 1216 contains a rotatable device in one or in both lobes, in accordance with some embodiments of the invention. FIG. 12B shows a rotatable device 1218A in lobe 1210 and a rotatable device 1218B in lobe 1212. It is to be understood however that device 1200E may comprise one rotatable device or two.

Lobes 1210 and 1212 are open to each other, in the sense that fluid communication between them is possible along at least a portion of their length.

Lobes 1210 and 1212 are sized and shaped with respect to helical devices 1218A and 1218B in such a way that devices 1218A and 1218B are independently rotatable each within its lobe. Optionally, devices 1218A/B are able to independently advance and retract each within its lobe. In some embodiments, a 'shoulder' 1220, or other similar formation, prevents devices 1218A and 1218B from moving 'sideways' from one lobe into another.

In some embodiments, devices 1218A and/or 1218B can be rotated in the directions shown by the small arrows in FIG. 12B: clockwise in lobe 1210 and/or counterclockwise in lobe 1212. In some embodiments, both can be rotated in directions opposite to those shown in the figure, i.e. counterclockwise in lobe 1210 and/or clockwise in lobe 1212. These directions cause portions of devices 1218A and/or 1218B which approach each other within their common lumen 1216 to approach a parallel movement where they are closest together, and then to pull apart.

Alternatively, in some embodiments devices 1218A and 1218B can be rotated in opposing directions (i.e. clockwise in both lobes or counterclockwise in both lobes). The two devices 1218A and 1218B can be moved in opposing directions where they are at their closest approach. Additionally, in some embodiments one or both rotatable devices can be caused to alternate rotational direction.

In some embodiments, devices 1218A and 1218B are helical devices (also designated 1218A and 1218B. Optionally, if device 1200E is inserted in an intestine, rotation of a helical device in one direction may serve to pull matter towards the intestine. Optionally or additionally, rotation in the opposite direction can serve to pull matter away from the intestine. Rotating one helical device in a direction which pulls matter towards the intestine and/or rotating the other in a direction which pulls matter away from the intestine may create shearing forces which may contribute to graining of matter caught between the helices.

In general, that diversity of movements described above (pulling towards intestine or away, rotating to create parallel movement or opposite movement, and independently moving helices or other rotating devices forward and backward in their lumen) create pulling, pushing and/or cutting forces which can serve to cut, grind, and otherwise grain material within lumen 1216.

In an exemplary embodiment of the invention, the shredding of pieces of fecal matter to a relatively small size is controllable and/or settable, for example, to an average size of less than 0.1 mm, less than 1 mm, less than 3 mm, less than 5 mm, or other smaller, intermediate or larger average sizes are used. Optionally, the matter crushing elements (e.g., devices 1218A and/or 1218B) are selected to result in shredding fecal matter to a selected average size, for example, the distance between threads is selected. Alternatively or additionally, one or more cleaning parameters are adjusted and/or controlled (e.g., automatically by a controller, manually by a user) to result in the average size of shredded particles, for example, the rate of rotation of the crushing elements.

Figure 12C:
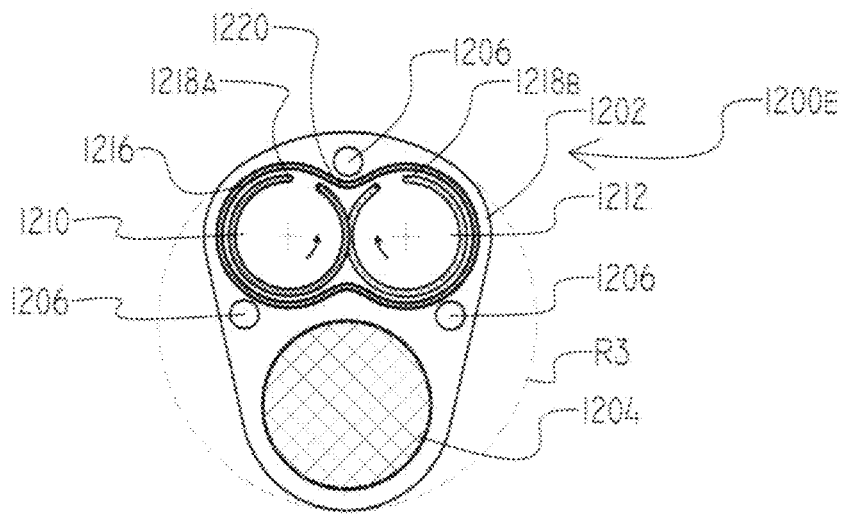

In some embodiments, additional graining effects can be produced when helical devices 1218A and 1218B are caused to overlap, as is shown in FIG. 12C. Overlapping helical devices can provide efficient pumping action and/or can also contribute to shredding the content of lumen 1216.

Helical devices 1218A and 1218B can be helical springs, can be rods and/or pipes surrounded by a helical thread, can be formed as a helical brush similar to those used to clean colonoscope working channels, and/or can be a wire or a rope wire made from stainless steel or another material.

Components having forms other than helical can also be used in one or both of lobes 1210 and 1212. An example is given in FIG. 12D, where two paddle-shaped forms 1222A and 1222B are provided in place of helical devices 1218A and 1218B. Rotating paddles create turbulence which generates shearing and/or tearing forces. Other shapes may also be used, and labels 1222A and/or 1222B should be understood to refer to these shapes also. In general any shape may be used which provides turbulence within lumen 1216 and/or which tends to propel materials proximally within lumen 1E.

Figure 12D:
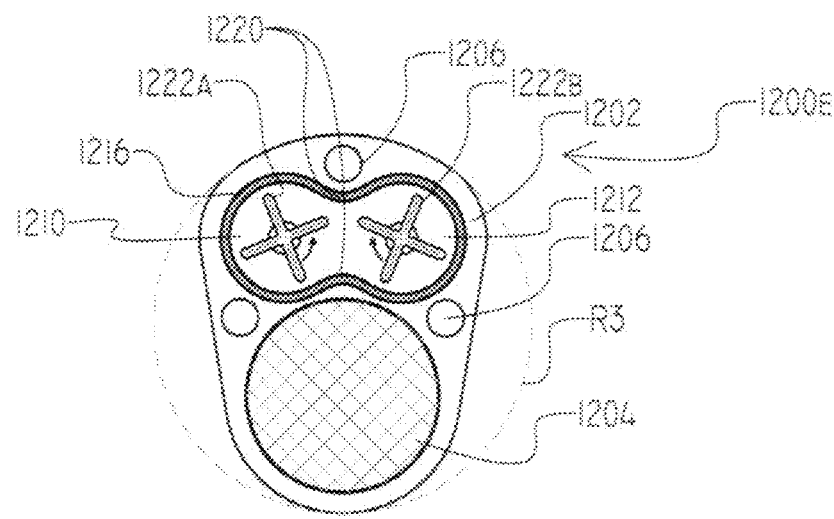

In some embodiments of the invention, the shapes used in lumen 1216 vary along the length of the lumen. For example, a paddle shape as shown in FIG. 12D could be provided at a distal end of lumen 1216, a propeller shape could be provided distal to the paddle shape along the same axes of lobes 1210 and 1212, and/or a helical device could be provided at more proximal portions of those lobes. If we refer to all these shapes extending the length of lobes 1210 and 1212 as "driving devices", then in some embodiments device 1200E may be provided with a variety of driving devices from among which a user may select the combination to be used depending on characteristics of the patient or any particular desired effect or desired effect of the cleaning process. In general, in some embodiments each driving device is free to rotate within its lobe and/or may be free to independently advance and retract within its lobe, yet each driving device is constrained so that a longitudinal axis of each driving device is retained (by the shape of lumen 1216) within one of the lobes.

Figure 12E:
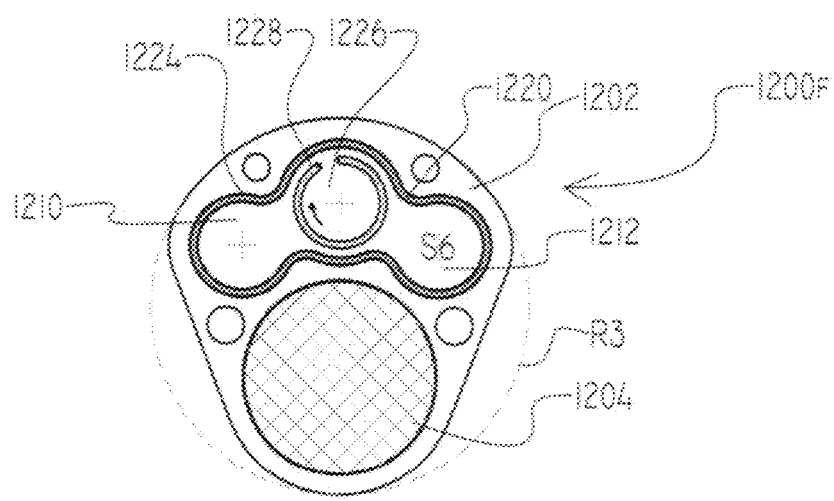

FIG. 12E provides an additional alternative embodiment, wherein more than two lobes are used in an exhaust conduit 1224, in accordance with some embodiments of the invention. Note that in these embodiments as well as in the other embodiments shown in FIGS. 12A-12F, each lobe may contain a driving device, or alternatively only some lobes may comprise a driving device and others may be empty of devices and available for the moving exhaust matter itself. FIG. 12E shows a central lobe 1226 which comprises a driving device (shown as a helical device 1228), while side lobes 1210 and 1212 are empty.

Figure 12F:
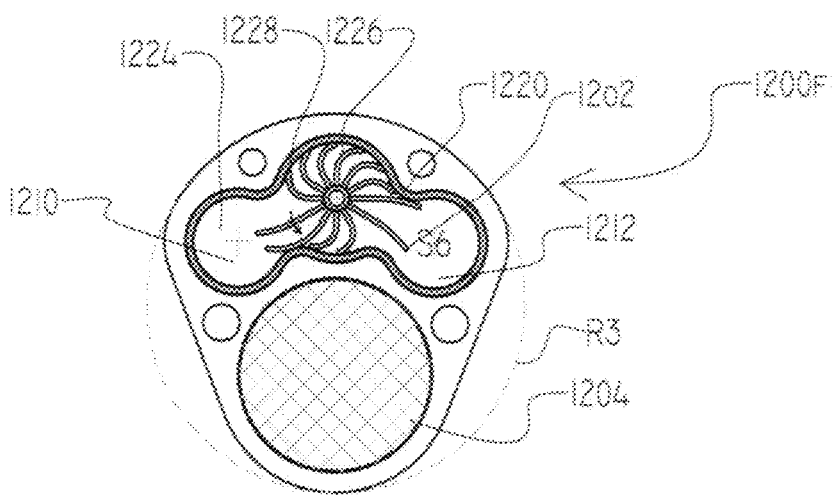

FIG. 12F shows an embodiment similar to that of FIG. 12E, but wherein a driving device is embodied as a rotatable brush 1230 within lobe 1226 but whose flexible bristles are long enough to penetrate into side lobes 1210 and 1212. Empty space is provided in lobes 1210 and 1212 to optionally facilitate transportation of objects out of the body, while also optionally providing a source for driving power and/or a source of turbulence and/or possibly shredding and/or cutting activities accomplished by bristles from brush 1230.

Using Multiple Conduits and Shaped Conduits to Reduce Overall Cross Section of a Cleaning Device In some embodiments, the device used to clean the colon passes the anal sphincter and/or a speculum to enter the colon. Once in the colon, the device may be maneuverable within the colon, which may includes several sharp curves. A device with reduced cross-section may be suitable for such a task.

Figure 12G:
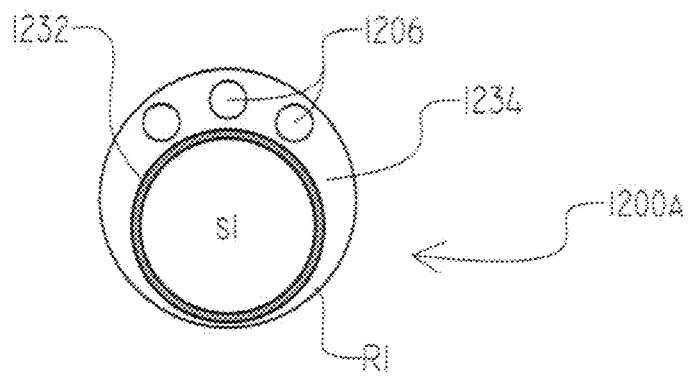
FIGS. 12G-12I present cleaning devices using multiple fluid input pipes and/or flattened exhaust lumens to reduce a cross-sectional area of the devices, according to some embodiments of the invention.
Figure 12H:
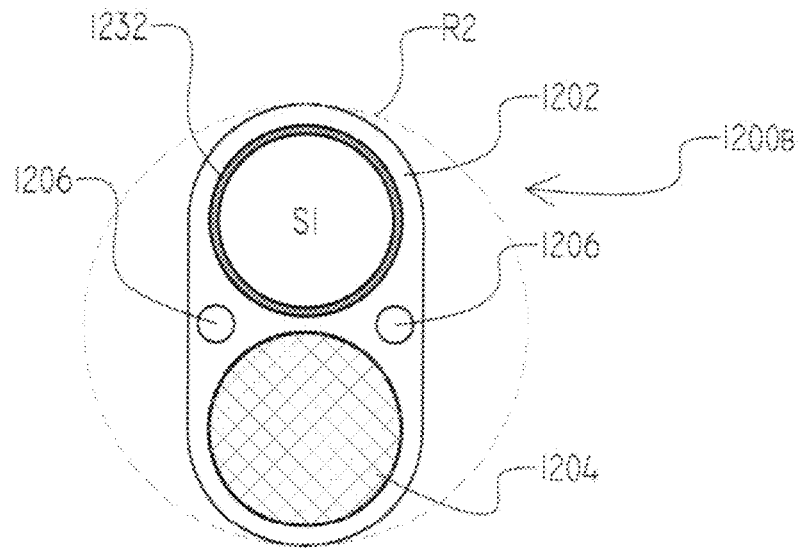
Figure 12I:
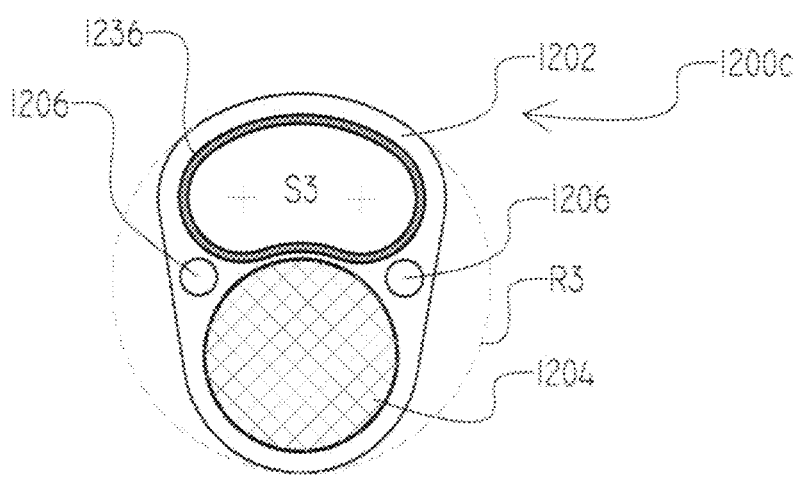

Attention is now drawn to FIGS. 12G-12I, which present cleaning device configurations in which multiple input conduits are used to reduce the device cross-section, according to some embodiments of the present invention. A cleaning device 10A presented in FIG. 12G comprises an evacuation lumen 1232 having a cross-section diameter S 1. A housing 1234 (for example an extrusion housing) comprises a plurality of fluid input conduits 1206 usable to introduce water into a colon. The overall diameter of device 1200A is R1. Evacuation lumen 1232 may comprise a matter transportation mechanism such as mechanism 513 discussed with reference to FIG. 2A.

FIG. 12H presents a cleaning device 1200B which comprises an endoscope or a colonoscope 1204. Endoscope 1204 is constructed together with, or attachable to, an evacuation lumen 1232 having a cross-sectional diameter S1. A housing 1202, optionally an extrusion housing, comprises a plurality of fluid input conduits 1206 usable to insert water into a colon. The maximum diameter of device 1200B is the diameter of circle R2 seen in FIG. 12H. Evacuation lumen 1232 of FIG. 12H is shown as identical in diameter to evacuation lumen 1232 shown in FIG. 12G, yet overall device diameter (the diameter of circle R2 of FIG. 12H) is greater than overall device diameter (the diameter of circle R1) of FIG. 12G. The diameter of a colon is limited, and a large-bore device like that shown in FIG. 12H could be problematic in several respects: it would tend to be stiff, difficult to steer, and could cause pain and retard recovery by damaging the intestinal wall of a patient.

FIG. 12I provides a device 1200C which comprises an endoscope 1204 and an evacuation lumen 1236 shaped as a flattened and slightly curved ellipse whose cross-section S3 is shown in the figure. Flattened lumen 1236 is advantageous over cylindrical lumen 1232 of FIG. 12H because an overall diameter of device 1200C (diameter of circle R3 of FIG. 12I) is smaller than the overall diameter (diameter of circle R2) of device 1200B, for an identical evacuation lumen cross-sectional area.

In an exemplary embodiment of the invention, a device comprises an evacuation lumen (e.g., lumen 1236) that is shaped according to the endoscope that it is being connected to (e.g., endoscope 1204). A potential advantage is to reduce a profile size of the combined device. For example, for a round endoscope 1204, the lumen is shaped as a flattened and slightly curved ellipse (e.g., crescent shaped), surrounding the endoscope, as illustrated in FIG. 12I. In an exemplary embodiment of the invention, the evacuation lumen comprises one or more indentations (e.g., shoulder 1220 as illustrated in FIGS. 12A-F) to prevent lateral migration and/or flailing of one or more matter removal devices (one or more non-limiting examples include; devices 1218A and/or 1218B, paddles 1222A and/or 1222B, helical device 1228) inside the curved evacuation lumen. A potential advantage of a relatively flattened design of the evacuation tube is a cleaning device using rotating forms to evacuate matter from the lumen, the device having a relatively low profile.

Cleaning Module with Rod Filter

Figure 3D:
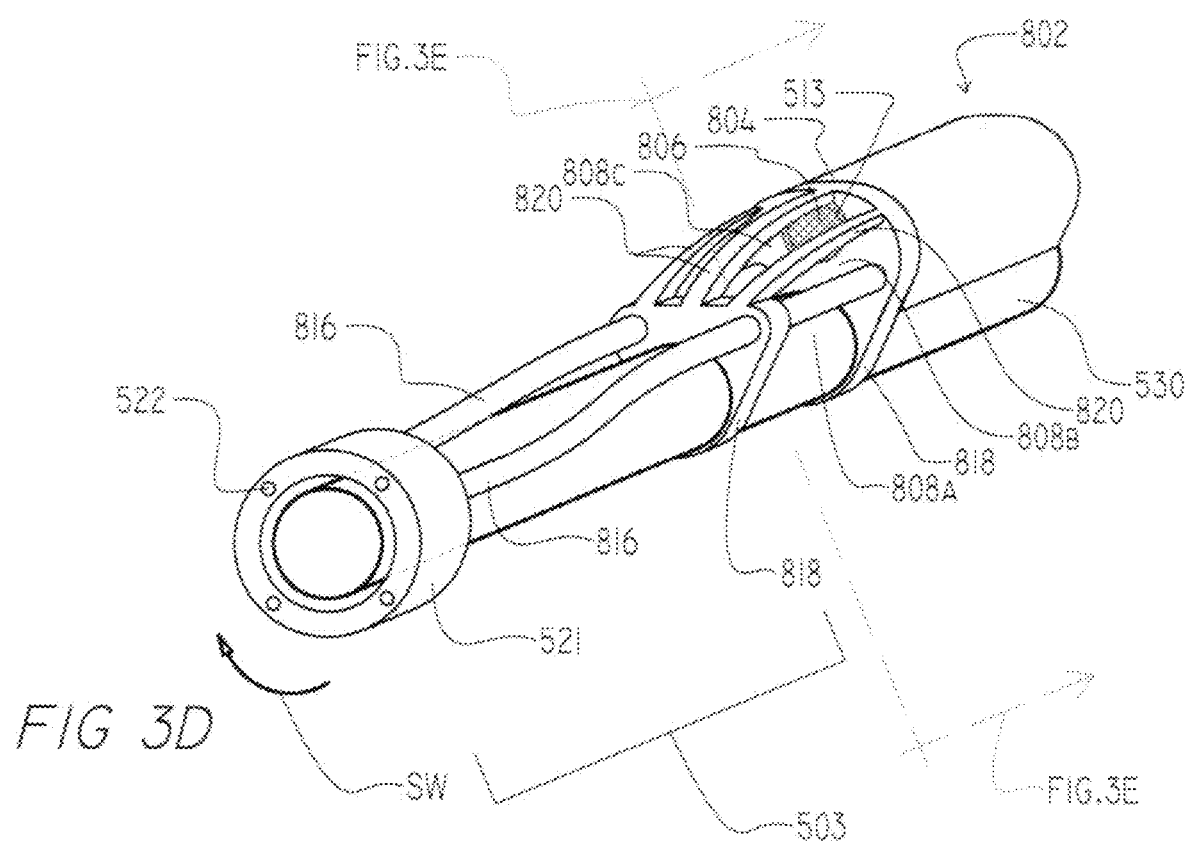
FIGS. 3D-3E are simplified schematics of colon cleaning systems with a filter, according to some embodiments of the invention.
Figure 3E:
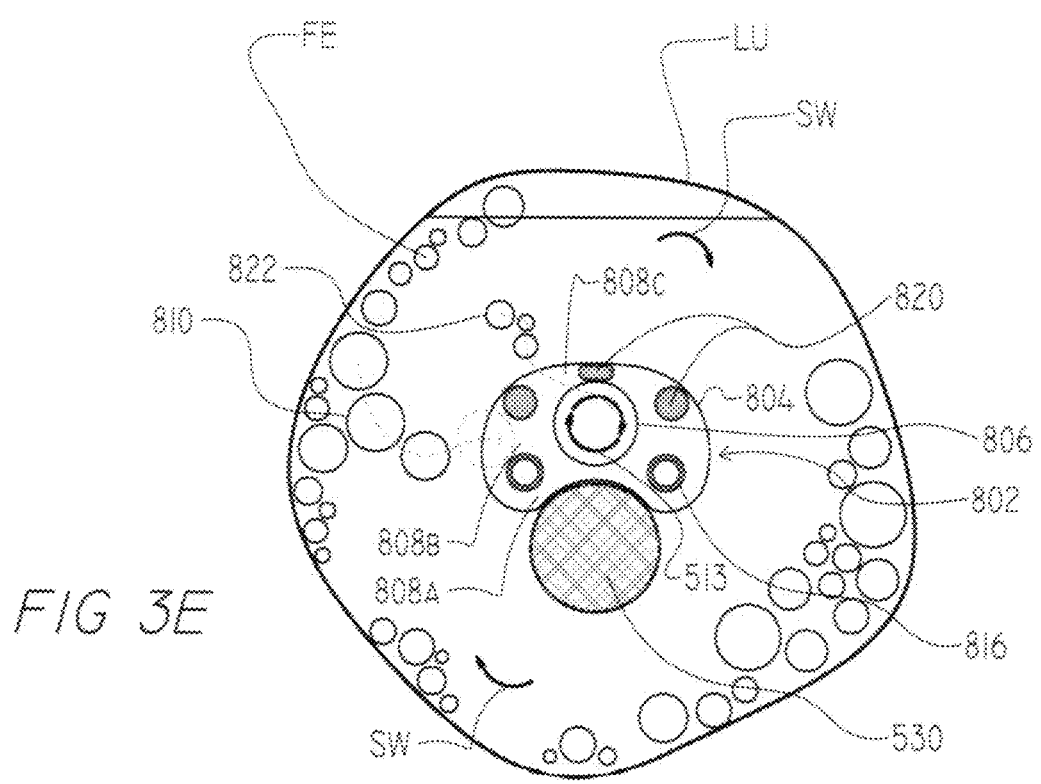

Attention is now drawn to FIGS. 3D (isometric view) and 3E (cross sectional view inside a fluid filled colon) of an endoscopic cleaning device 802 which comprises a filter 804, in accordance with an exemplary embodiment of the invention. Filter 804 reduces and/or prevents blockage of an output conduit 806 during cleaning by matter such as feces. Optionally, filter 804 is dependent on device 804 being coupled (e.g., by attachment elements 818 such as bands) to colonoscope 530, for example, colonoscope 530 forms a barrier and/or wall to a large gap in filter 804.

In an exemplary embodiment of the invention, filter 804 comprises a plurality of openings 808A-C to allow water and/or waste matter to pass through into conduit 806. For example, 2, 6, 10, or other smaller, intermediate or larger number of openings are used. A potential advantage of using a plurality of openings, is if one or more openings are blocked by feces, one or more openings will remain unblocked to allow the cleaning process to continue.

In an exemplary embodiment of the invention, openings 808A-C have at least one dimension that is relatively smaller than the diameter of output conduit 806, for example, dimension of openings 808A-C is 3 mm-5 mm for a diameter of conduit 806 of 8 mm, or other smaller, intermediate or larger combinations are used. The dimensions and/or the relationship between the dimensions of openings 808A-C and/or output conduit 806 are selected to prevent relatively large fecal pieces 810 from entering and obstructing outlet conduit 806. Additionally, dimensions and/or the relationship between the dimensions is selected to allow relatively small fecal pieces 822 to pass into a relatively larger output conduit 806 without obstructing conduit 806. Optionally, feces are shredded and/or ground into relatively smaller particles inside output conduit 806 such as by rotational apparatus 513.

In an exemplary embodiment of the invention, opening 808A is formed between colonoscope 530 and at least one pipe 816 supplying fluid to at least one fluid input conduit 522. Opening 808B is formed between pipe 816 and strut 820. Opening 808C is formed between struts 820. Struts 820 are substantially parallel to the long axis of device 820, forming openings 808A-C that are substantially parallel to the direction of motion (e.g., forward and/or reverse). In some embodiments, the substantially parallel struts and/or openings have an angle of no more than 45 degrees relative to the long axis, or no more than 30 degrees, no more than 15 degrees, or other smaller, intermediate or larger angles are used. Other embodiments of filter 804 that serve similar functions can have different sized and/or shaped openings, and/or be formed by different structural elements. For example, filter can be a screen over the opening to conduit 806.

In an exemplary embodiment of the invention, motion (e.g., forward, reverse, sideways) of device 802 during the cleaning process serves to loosen and/or dislodge feces trapped in openings 808A-C (e.g., into conduit 806 or outside of filter 804), for example, using frictional forces created between the colon wall and trapped feces. A potential advantage of openings 808A-C being substantially parallel to the direction of motion of device 802 is aiding in loosening and/or dislodging the trapped feces.

In an exemplary embodiment of the invention, filter 804 prevents and/or reduces contact between the colon wall and rotational apparatus 513. Optionally, apparatus 513 is located sufficiently far from openings 808A-C, for example, a distance of about 5 mm, 10 mm, 15 mm away, or other smaller, intermediate or larger distances. Alternatively or additionally, apparatus 513 is positioned to be substantially perpendicular to the colon wall during cleaning. Alternatively or additionally, size of openings 808A-C is sufficiently small to keep colon tissue outside of filter 804.

Swirling Liquid Motion Produced by Circularly Directed Water Jets

Attention is now drawn to FIGS. 4A-4F, which present an endoscopic cleaning device 540 which comprises a set of water spray nozzles 542 arranged around at least a portion of a circumference of a conduit 544. In some embodiments of the invention, the cleaning device comprises a tip 541 having a set of nozzles 542, each nozzle of the set is aimed in a direction which imparts to a jet of liquid issuing through it, a direction having a directional vector which has a vector component not parallel to the longitude axis vector of cleaner 540.

Such a jet might have a vector comprising at least 2 subvectors wherein (a) is a subvector collinear or parallel with the longitude axis of cleaner 540 and (b) is a subvector tangent to the circumference of tip 541. A workstation (not shown) supplies pressurized fluid via pipe 543 to tip 541. Optionally, tip 541 houses an internal manifold which distributes the pressurized fluid to nozzles 542. FIG. 4C shows a front view of the device 540 positioned within a colon. Straight arrows on the figure show potential directions of the water jets from nozzles 542. Curved arrows on the figure show the potential direction of an induced swirling motion of liquid filling a section of the colon. FIG. 4D shows a schematic isometric view of the tip 541 showing directions of jets [JE] which generate the swirl/rotation effect [RO] shown in the figure. FIG. 4D may be contrasted with FIG. 4E which shows a tip comprising a set of nozzles. The nozzles in FIG. 4E are aimed in a direction which imparts to a jet of liquid issuing through it in a direction having a vector V[J] collinear or parallel to the longitude axis vector V[E]. Such design of nozzles may generate a forward motion of fluids within a colon lumen and/or produce turbulence within the lumen's fluids, but may not produce a swirl or rotation effect around the longitude axis of the endoscopic device.

Figure 4A:
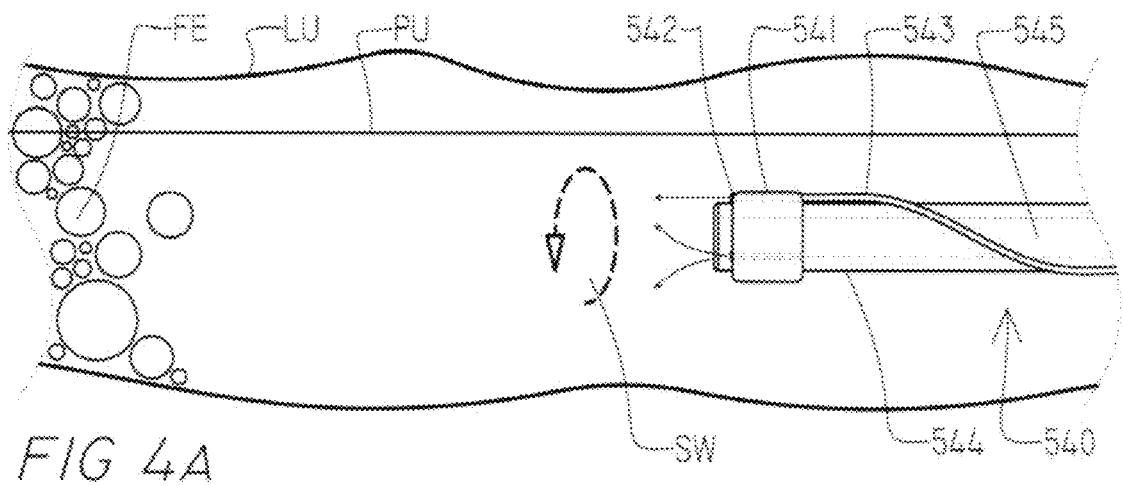
FIGS. 4A-4D and 4F are simplified schematics of features of a colon cleaning system designed to induce a swirling motion in liquids filling or partially filling a colon, according to some embodiments of the invention.
Figure 4B:
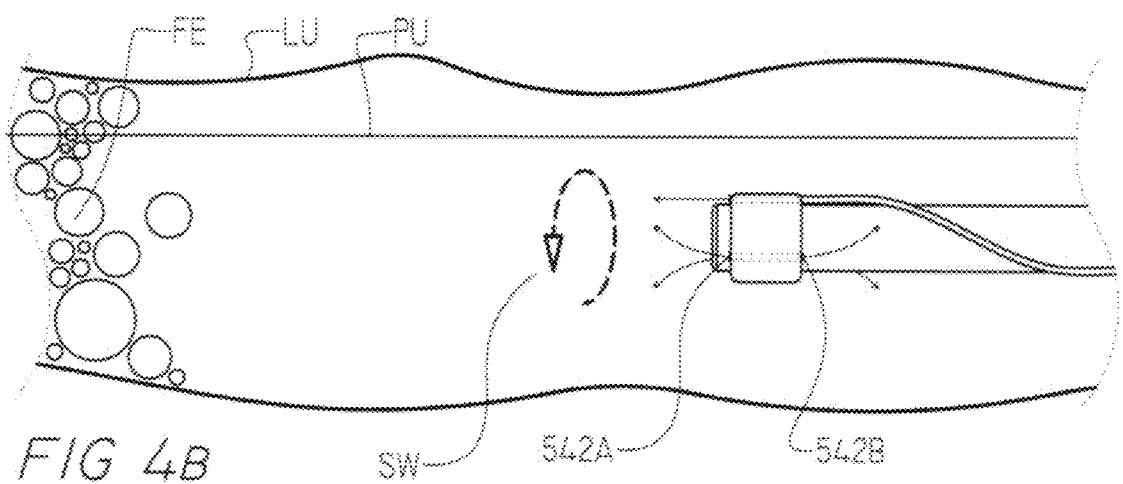
Figure 4D:
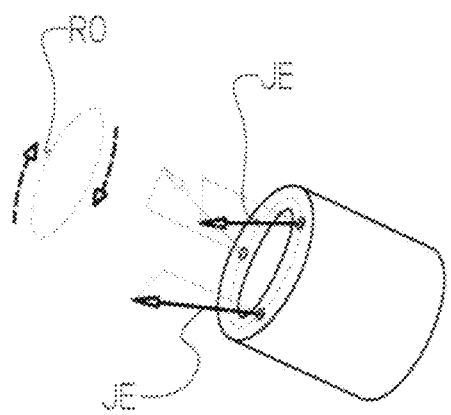
Figure 4C:
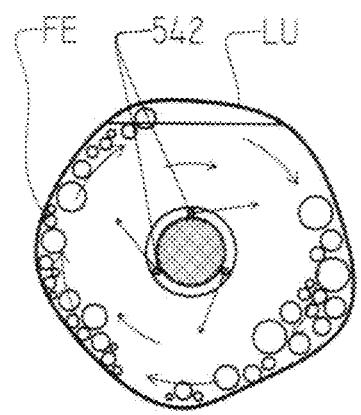
Figure 4E:
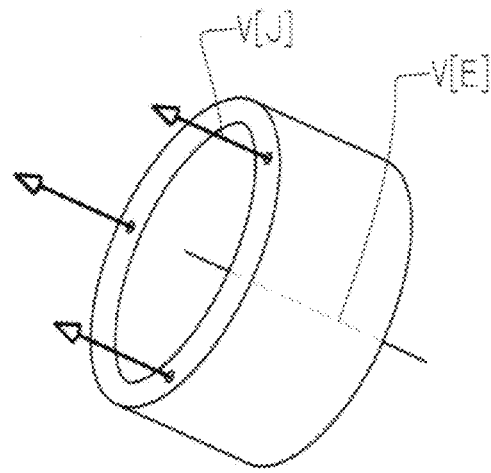
FIG. 4E is a schematic of a simple nozzle system.
Figure 4F:
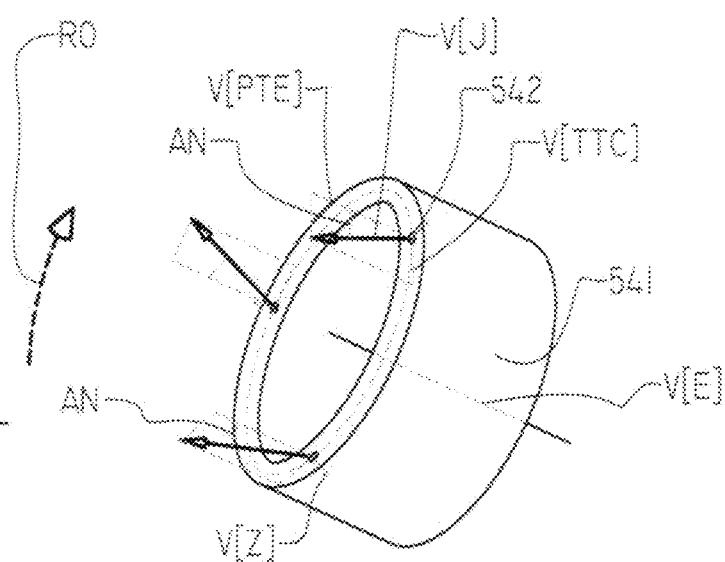

FIG. 4F is an additional view of tip 541 as shown in FIG. 4D. FIG. 4F shows a set of nozzles aimed in a direction which imparts to a jet of liquid issuing through it in a direction having a vector V[J] not collinear or parallel to the longitude axis vector V[E] of cleaner 540. Jet direction V[J] comprises two vectors;

(a) Vector V[PTE] (Parallel To Endoscope axis) is a vector parallel to the longitude axis vector V[E] of cleaner 540 and;
  (b) Vector V[TTC] (Tangent To Circumference) is a vector tangent to the circumference of endoscopic device's tip 541, and consequently perpendicular to a longitudinal axis of the device.

Addition of those two vectors produces vector V[J] {V[PTE]+V[TTC]=V[J]}. The angle between vector V[J] and vector V[PTE] is marked in the drawing as (AN). This angle could vary between 10°-90°, with best cleaning results expected between 30°-60°.

In the paragraph above a single jet direction is described, but tip 541 may comprise a plurality of jets, as shown in FIG. 4F. Optionally, each jet is aimed in a similar manner with respect to its own position on the tip circumference.

In FIG. 4F angles (AN) of each of the 3 jets are shown as being equal, but in alternative embodiments there may be variations in the angles AN of each of the jets. In some embodiments jet vector V[J] comprises vectors V[PTE] and V[TTC] as described, and an additional vector V[Z] perpendicular to V[PTE] and V[TTC]. Such jets could be set in a polar array around the longitude axis of the endoscopic device 540. The arrangement may generate an enhanced swirling effect, for example, relatively improved cleaning results.

When fluid is supplied under pressure and sprays through nozzles 542 and passes into a fluid filling the colon, the effect is to agitate (e.g., impart a rotating and/or swirling motion) the colon-filling fluid (which is also likely to comprise swirling chunks of fecal matter). This swirling liquid may dislodge fecal matter adhering to the colon walls, producing the cleaning effects described above.

In an embodiment shown in FIG. 4A, fluid jets are directed forward from the distal end of cleaner 540. In an embodiment shown in FIG. 4B, jets are directed in both distal and proximal directions.

FIG. 4C shows nozzles 542 embedded in a nozzle ring 541, which may be a full circular ring, a partial circle, or may have some other form, but which comprises a plurality of nozzles designed to work in coordination.

In some embodiments of the invention, jets of liquid from nozzles 452 are directed to work in coordination with other liquid swirling mechanisms such as rotating apparatus 517 (e.g., FIGS. 2A-2J). For example, the liquid pressure, liquid velocity and/or angles of nozzles 452 are selected to have an additive effect in creating relatively improved (e.g., stronger, faster) liquid swirling in the colon when used together with rotating apparatus 517, such as compared to the use of nozzles 452 or apparatus 517 alone.

Backward-Pointing Water Jet

Figure 5A:
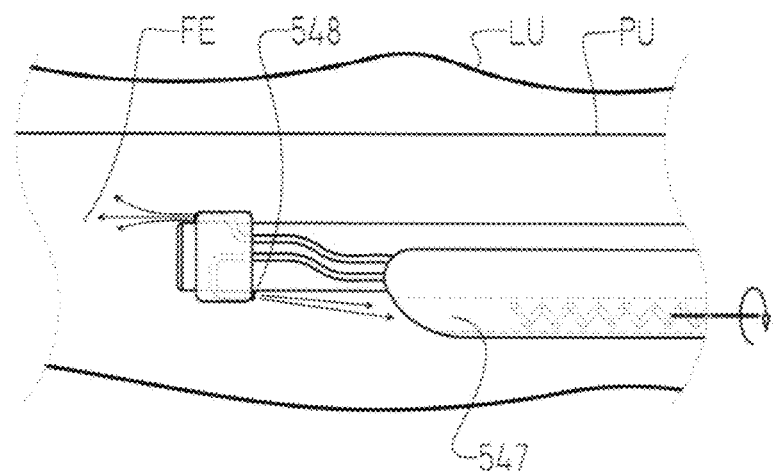
FIG. 5A is a simplified schematic of a colon cleaning system comprising a water jet for cleaning the intake port of an evacuation conduit, according to some embodiments of the invention.

Attention is now drawn to FIG. 5A that comprises at least one nozzle 548 aimed backwards (i.e. proximally), and which generates a jet that flows into the opening of the output conduit 547. Such a jet can assist in forcing fecal matter into the distal opening of conduit 547 and/or can serve to keep clean the distal end of conduit 547, which might otherwise tend to get blocked by accumulated fecal debris.

Cleaning Systems with Cameras

Figure 5B:
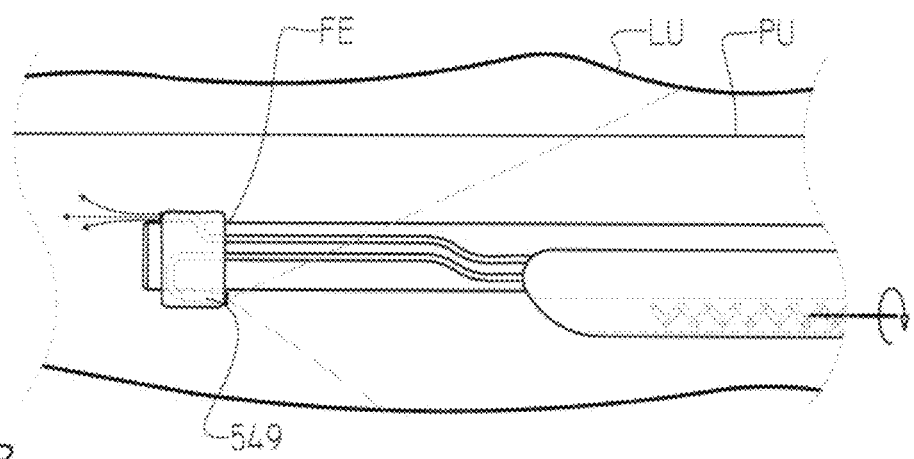
FIGS. 5B and 5C are simplified schematic of a colon cleaning system comprising a camera, according to some embodiments of the invention.
Figure 5C:
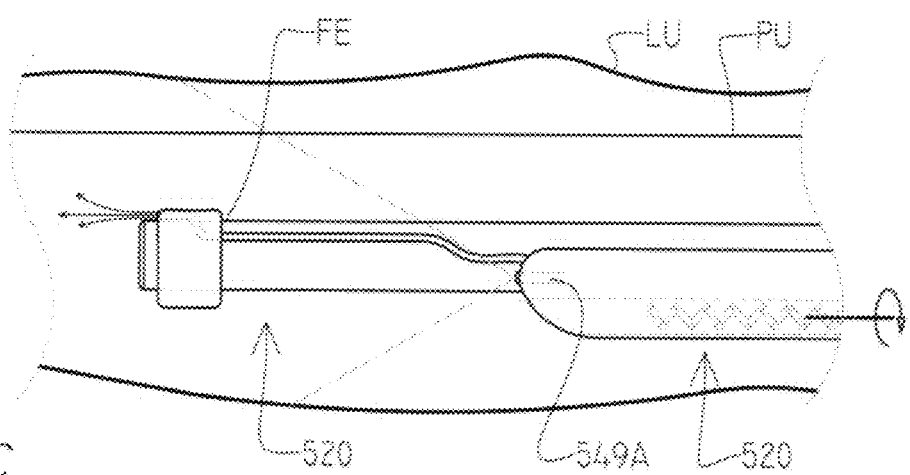

FIG. 5B presents an embodiment which comprises a camera 549 positioned to provide images in a proximal direction. In the embodiment shown in the figure, the distal entrance to exhaust pipe 547 is within view of camera 549. Camera 549 can also be positioned to provide other proximal views. Camera 549 can be coupled with LED illuminating light sources In FIG. 5C, a camera 549A is provided on cleaner 520 looking forward toward the distal end of endoscope 530 to which it is attached. Cameras 549 and 549A may be provided in addition to a camera 504 provided in endoscope 530, providing a secondary viewpoint useful, inter alia, in detection of polyps which may lie hidden in a fold of the intestinal wall.

Cleaning Systems with Turbines

FIGS. 6A-6C present several embodiments in which a "turbine" is provided within an evacuation conduit such as conduit 512 described above. As used herein, a "turbine" is defined as a rotating helical device contained within an outer casing. Turbines of this description are potentially useful in shredding lumps and chunks of fecal matter which might otherwise block or impede flow within a conduit 512 or similar conduit, and/or can in some cases may provide more forceful suction than might be provided by a standard helical device. Turbines are also potentially advantageous in that friction between the outer surface of the turbine and body conduit is relatively low, potentially enabling such a turbine to be advanced or retracted within the conduit with relative ease.

FIG. 6A shows a turbine 551 used together with (and in this exemplary embodiment, distally attached to) a helical apparatus 552. FIG. 6B shows a turbine 551 connected to a connector 553, which may be a rope wire, or other kind of wire, or a flexible rod. Each of these can power rotation of turbine 551 by transmitting rotation motion to turbine 551 from an external motor (not shown). FIG. 6C shows how several turbines (551A and 551B in the figure) may be interconnected with a cable or a flexible rod.

Pulsing Systems

Attention is now drawn to FIGS. 7A-7F, which present apparatus used to inject into the colon a sequential combination of fluids in which fluid of a first kind alternates relatively rapidly with fluid of a second kind. In some embodiments, a first fluid (A) comprises water, purified water, saline, and/or water with supplemental materials such as soap, and a second fluid (B) comprises of gas or aerosol, wherein non-limiting examples of gas include $CO_2$, pressurized room air or other gas mixtures. In some embodiments fluids A and B are caused to flow within an input conduit in alternation, agitating the fluid and/or feces inside the colon segment. Potentially relatively improved cleansing results are produced.

Figure 7A:
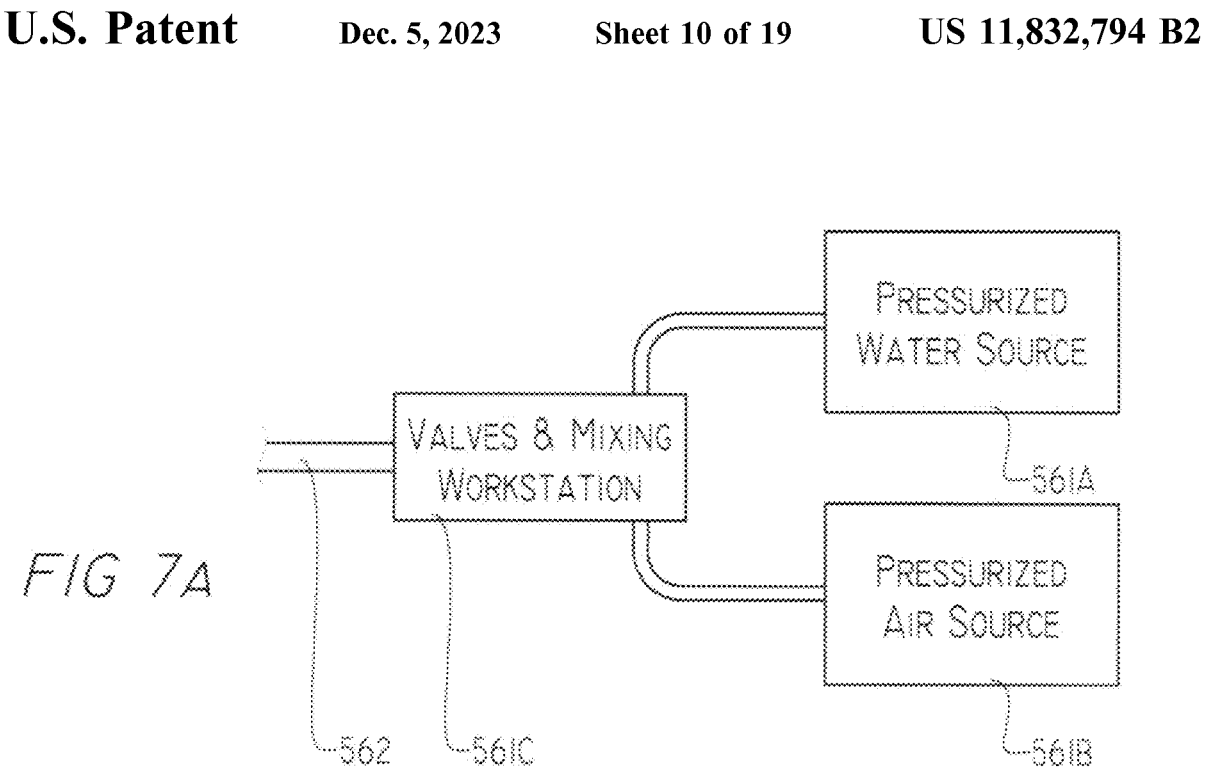

FIG. 7A shows a fluid source module appropriate for providing fluids in such a sequential combination. Valves and mixing workstation 561C receives pressurized fluid A from source 561A and pressurized fluid B from source 561B. Valves and workstation 561C comprises computer-controlled electrical valves, or any other valve or orifice configuration to supply an alternating sequence of fluids to conduit 562, which may connect, for example, to a cleaner input conduit such as conduit 501 and/or conduit 511B, both discussed above.

In an exemplary embodiment of the invention, the system illustrated in FIG. 7A is used to supply a mixture of fluids A from source 561A and fluid B from source 561B to conduit 562. Optionally, mixing is passive, for example, operating in a manner similar to a carburetor based on the Venturi effect. Alternatively or additionally, mixing is active, for example, control (e.g., automatically by a controller, manually set by the user) of mixing proportions is achieved by valves that control flow of the fluids.

Figure 7B:
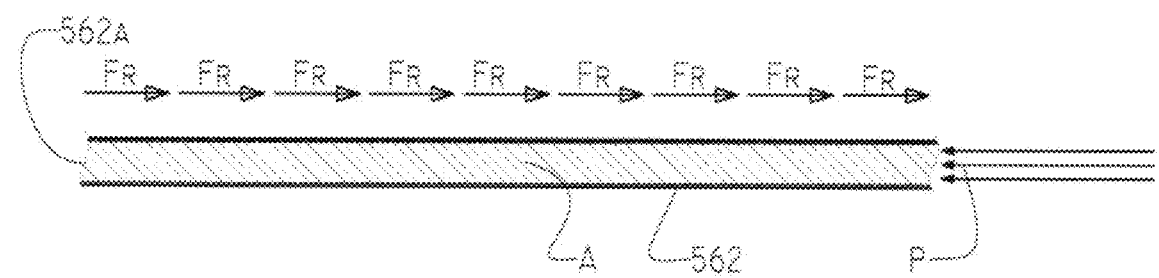
FIG. 7B is a simplified schematic showing friction resistance to fluid flow within a conduit.

FIG. 7B shows flow of fluid A within a pipe 562, the flow due to the external fluid pressure (P) supplied from workstation 561C. Fluid flow within a pipe potentially generates a friction force that correlates inter alia with the length of the pipe. This friction is represented in FIG. 7B by the small arrows marked "Fr" along the length of the pipe.

Figure 7C:
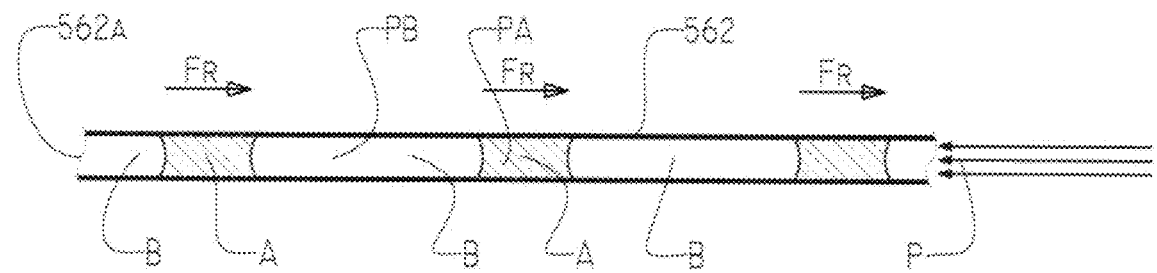

FIG. 7C shows the effect when workstation 561C presents a short supply burst of fluid A followed by a burst of fluid B in a cyclical manner, generating an alternating flow within the pipe, according to an embodiment of the present invention.

The lengths of pipe 562 are identical in FIGS. 7B and 7C, but potentially the friction-indicating arrows are quite different. Since fluid B is primarily a gas, it may have relatively negligible friction when flowing within the pipe (562). Fluid A, a liquid, may experience relatively more friction in the same pipe. Pressure within sections containing fluid A is marked "PA", and pressure within sections containing fluid B is marked "PB". The pressure of Fluid A (liquid) is 1.2 Bar, 2.2 Bar, 3.6 Bar, or other smaller, intermediate or larger values are used. The pressure of Fluid B is relatively higher than the pressure of Fluid A, 0.2 ATM higher, 0.5 ATM higher, 0.7 ATM higher, or other smaller, intermediate or larger values are used. Given the same conditions (e.g. same pipe length, same pipe inner diameter, and same inlet pressure) friction in the alternating cyclic flow as shown in FIG. 7C is lower than friction in the continuous flow of only fluid A as shown in FIG. 7B. Hence use of alternating fluid flow as taught above may result in relatively higher velocity of fluid A as it reaches pipe outlet 562A, under the method of FIG. 7C. On the other hand, when using this alternating cyclic flow, relatively lower amounts of fluid A may be transported in to the body.

It is noted that when injecting fluids into the human body it may be necessary to set upper limits to the amount of pressure used, such as for safety reasons. Standard medical practice provides an upper safety limit to the amount of pressure that may be injected into the body. For example, pressure should be below 100 mbar, below 76 mbar, below 50 mbar, or other smaller, intermediate or larger pressure thresholds are used. The method shown in FIG. 7C, comprising alternating rapidly between supplying fluid A and supplying fluid B, may engender a higher velocity delivery of fluid A, without exceeding safety limitations on the amount of pressure supplied. Such higher-velocity intermittent delivery of fluid A is highly appropriate and useful in a jet used for dismantling chunks of feces, for example. Consequently a cleaning system utilizing a fluid source as shown in FIG. 7A and producing a flow as shown in FIG. 7C may present relatively better cleaning results, without using relatively higher water pressures.

Illustrated in FIGS. 7D-7F are successive stages in use of a device (560) that comprises an inlet pipe (562) and an outlet pipe (not shown). The inlet pipe is supplied with the alternating cyclic flow as described above, provided from a workstation (not shown).

Consider what happens when pressure of the fluids in inlet pipe 562 is set, for example, to 2 ATM, assuming that the pressure of fluids filling the colon (P.CO) is set in the normal range of 1 ATM. When a portion of fluid A under 2 ATM pressure is contained within the pipe's tip 562B as shown in FIG. 7D, flow of fluid A may be smooth. Since fluid A is composed primarily of water, it may not expand appreciably when ejected into a colon filled with water and fecal matter at 1 ATM pressure (P.CO). As shown in FIG. 7E, a small shock wave 563A will potentially be generated due to the flow of a portion of fluid A into the colon lumen.

When fluid A completely exits the pipe's tip 562B as illustrated in FIG. 7F, the portion of fluid B following may be free to burst out of the pipe's outlet. Fluid B, primarily a gas (at 2 ATM pressure in this exemplary embodiment), expands rapidly to double its volume in the 1 ATM pressure of the colon. This sudden gas expansion generates a relatively big shock wave, shown in FIG. 7F as 563C.

In an exemplary embodiment of the invention, at least some of the gas and/or other fluids (e.g., fluids A and/or B) are discharged by the patient in the natural manner through the anal sphincter, for example, preventing a build-up of excess gas and/or fluids. Alternatively or additionally, discharging occurs through an output conduit (e.g., conduit 512).

This alternating cyclic flow system can result in one or both of two advantageous outcomes when working in a colon full of water & fecal matter:
  (i) It provides a means for producing a high-powered jet while yet limiting the pressure to which the human body is exposed. This effect can be used both in a colon filled with water and in a colon filled with air or other gas.
  (ii) Vibration inside the colon caused by cyclic shockwaves like 563C shown in FIG. 7F enhance the jet's ability to break down fecal matter into small parts and helps "peel" fecal matter from the colon wall. This effect is primarily useful in a colon full of water and fecal matter. Unlike water jets, which work in a directional way and therefore have a directionally limited effect, the rapid repetitive effect of shockwaves 563C is omni-directional, and therefore produces rapid widespread cleaning results while largely eliminating the need for carefully directed steering of the cleaning tool by an operator. In other words, the system does relatively better cleaning and is relatively easier to use.

Exemplary Control System

Figure 10:
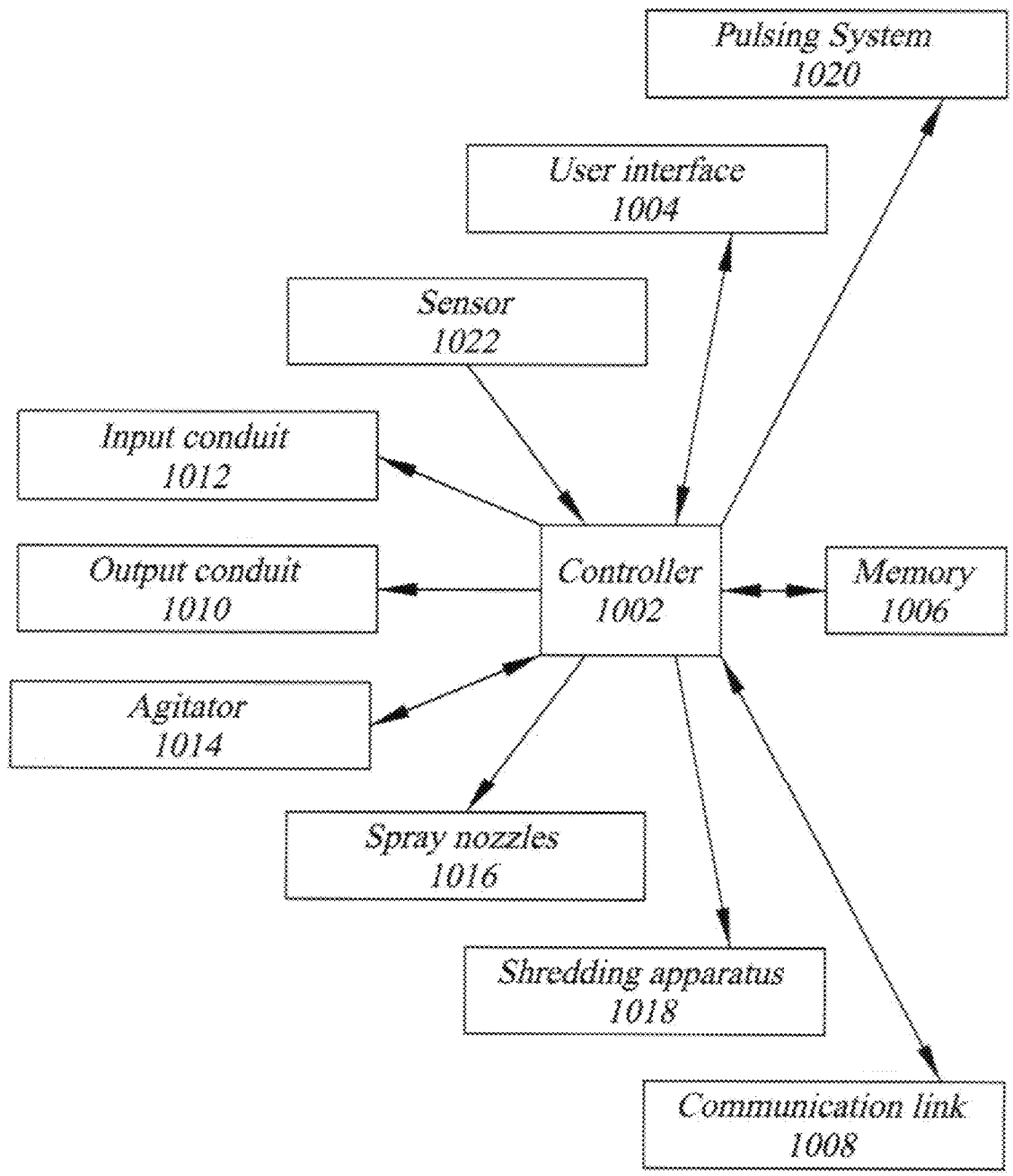
FIG. 10 is an exemplary control system for cleaning the colon, in accordance with an exemplary embodiment of the invention.

FIG. 10 illustrates an exemplary control system 1000 for cleaning body cavities such as the human colon, in accordance with an exemplary embodiment of the invention. System 1000 provides for the control and/or monitoring of the cleaning.

In an exemplary embodiment of the invention, an operator (e.g., physician performing the procedure) programs a controller 1002 (e.g., computer) for cleaning using a user interface 1004 (e.g., keyboard, mouse, monitor). Optionally, treatment is monitored, for example, by viewing feedback parameters on interface 1004.

In some embodiments of the invention, interface 1004 provides feedback about the cleanliness of the colon segment. Non-limiting examples of the feedback include; signaling to the physician performing the procedure to check the cleanliness of the colon segment, signaling that the colon segment has been cleaned and optionally proceeding to the next colon segment (e.g., asking for permission from the user to advance). Optionally, the cleanliness of the colon segment is checked by a user and/or sensor, non-limiting examples include; the physician visually inspecting the segment (e.g., using optical equipment), a sensor measuring the opacity of the fluid being removed from the segment. Optionally, the feedback is provided to controller 1002, for example, controller 1002 signals the device to continue functioning until the colon has been sufficiently cleaned.

In an exemplary embodiment of the invention, controller 1002 is coupled to a memory 1006, for example, memory 1006 is stored thereon, memory 1006 is stored on user interface 1004 and/or memory 1006 is remotely accessible, for example, by a communication link 1008 (e.g., wireless and/or wired connection).

In an exemplary embodiment of the invention, the cleaning is controlled by controller 1002 according to logic (e.g., a software module), for example using a data table. Optionally, the table is stored on memory 1006. In an exemplary embodiment of the invention, the table contains at least one cleaning parameter, optionally correlated with one or more other parameters, for example, according to clinical indications. Optionally, the cleaning parameters are based on trial and error, for example, empirical data collected from the patient currently being cleaned with the colon cleaning device (e.g., during the cleaning) and/or previously collected from a group of patients such as part of a study in patients have similar clinical indications. Optionally or additionally, one or more functions and/or parameters are selectable (e.g., manually set by a user, automatically selected by software).

In an exemplary embodiment of the invention, controller 1002 is coupled to one or more elements such as:
  Output conduit 1010 for removing fluids and/or feces from the colon, for example, output conduit 512 as described with reference to the section "Filing the colon with liquid, swirling the liquid".
  Input conduit 1012 for inserting fluids into the colon, for example, input conduit 511A as described with reference to the section "Filing the colon with liquid, swirling the liquid".
  Agitator 1014 for agitating the liquid in the colon (e.g., swirling, vibrating), for example, rotating apparatus 517 as described with reference to the section "Filing the colon with liquid, swirling the liquid".
  At least one spray nozzle 1016 for agitating the liquid in the colon, for example, water spray nozzles 542 as described with reference to the section "Swirling liquid motion produced by circularly directed water jets", and/or nozzle 548 as described with reference to the section "Backward pointing water jet".
  Shredding apparatus 1018 for shredding the feces, for example, rotatable device 1218A/B as described with reference to the section "Exemplary embodiments for graining and/or exhausting fecal matter".

Pulsing system 1020 comprising a mechanism for mixing and/or alternating a pressurized liquid source and a pressurized air source, for example, as described with reference to the section "Pulsing systems".

At least one sensor 1022, for example, for measuring input flow rates (e.g., fluid meters 600A and/or 600B), output flow rates (e.g., scales 608 and/or 608A), for determining fluid levels (e.g., sensor 736).

One or more non-limiting examples of settable parameters include:

Cleaning efficiency—is the amount of waste and/or feces removed from the colon during cleaning, for example, at least 90%, at least 95%, at least 99%, about 100%, or other smaller, intermediate or larger percentages are used. In some embodiments, cleaning efficiency is estimated by analyzing the fluid removed from the colon, for example, by a sensor analyzing the opacity of the removed fluid.

Rotation rate of the fluid in the colon—the axial rotation of the filling fluid and/or waste matter in the colon (e.g., portion thereof) caused by the rotational apparatus. For example, greater than 20 RPM, greater than 30 RPM, greater than 50 RPM, or other smaller, intermediate or larger values are used.

Percentage of the filling liquid rotating around a longitudinal axis of the colon portion—the axial rotation caused by the rotational apparatus. For example, greater than 40%, greater than 50%, greater than 75%, about 100%, or other smaller, intermediate or larger values are used.

Fluid pulsing parameters—for example, pressure of the pulsing liquid such as 1.2 bar, 2.2 bar, 3.6 bar, or other smaller, intermediate or larger values. For example, the volume of the pulse of liquid. For example, the frequency of the pulses of liquid.

Gas pulsing parameters—for example, pressure of the gas such as 1.2 bar, 2.1 bar, 2.4 bar, 3.6 bar, or other smaller, intermediate or larger values. For example, pressure of the gas relative to the pressure of the alternating liquid, such as larger by 0.2 ATM, 0.5 ATM, 0.7 ATM, or other smaller, intermediate or larger pressures. For example, the volume of the pulse of gas. For example, the frequency of the gas pulses.

Agitator rotation rate—rotation rate of the rotating element.

Agitator longitudinal vibration—frequency of vibration along the longitudinal axis (e.g., forward and backward motion).

Agitator rotational vibration—frequency of vibration caused during rotation of the rotation element (e.g., side to side motion substantially perpendicular to the longitudinal axis).

Size of shredded fecal matter—average size of particles once shredded.

One or more non-limiting examples of selectable parameters include:

Cleaning rate—is the rate of advancement of the colon cleaning device.

Liquid input rate—is the rate at which the cleaning fluid (e.g., water, saline) is inserted into the colon.

Output rate—is the rate of removal of the cleaning fluid along with any waste matter (e.g., feces) from the colon.

Colon fill proportion—is the amount of liquid in the colon (e.g., colon segment) during cleaning. Can be set to a constant value, or can be variable such as to maintain the cleaning device fully submerged in liquid.

Pressure of colon—ambient pressure during cleaning.

Colon pressure change—is the change in the ambient pressure of the colon (e.g., colon segment) during cleaning, relative to the pressure before cleaning.

Colon liquid rotation rate—rotation of the inserted liquid and/or feces caused by the rotation element and/or spray jets.

SOME EXAMPLES OF EXPECTED EFFECTS ASSOCIATED WITH VARIABLES

The following are some non-limiting examples illustrating some parameters under control, and their association with some expected treatment effects, in accordance with an exemplary embodiment of the invention:

Cleaning rate—In some embodiments, the cleaning rate is set (e.g., by the user) and the device advanced at the specified rate. Alternatively, the cleaning rate is a function of the cleaning parameters, and may vary by the amount of feces in the colon and/or other cleaning parameters (e.g., input and/or output flow rates, vibration). For example, at least 5 cm/min, at least 10 cm/min, at least 15 cm/min, or other smaller, intermediate or larger rates are used.

Liquid input rate—A faster liquid input rate results in a faster cleaning rate and/or higher cleaning efficiency. The liquid input rate is balanced by a suitable output rate to maintain a set colon fill proportion, and/or pressure in the colon.

Output rate—A faster output rate results in a faster cleaning rate and/or higher cleaning efficiency. The output rate is balanced by a suitable input rate (e.g., equal or greater rate, taking into account the removal of feces in the colon) to maintain a set colon fill amount, and/or pressure in the colon.

Colon fill proportion—A relatively higher colon fill proportion potentially results in a faster cleaning rate and/or a higher cleaning efficiency, for example, the 'swirling' and/or 'shocks' potentially remove and/or break down relatively larger amounts of feces.

Colon pressure—should be maintained within a threshold range in order to maintain a safe working pressure (e.g., reduce and/or prevent adverse events). Controlled at least in part by the input and/or output rates.

Change in colon pressure—positive and/or negative pressure swings should be maintained within a threshold in order to maintain a safe working pressure. Controlled at least in part by the input and/or output rates.

Pulsing parameters (gas and/or liquid)—may be used to create relatively smaller or relatively larger 'shock waves' in the colon, dislodging relatively larger and/or relatively smaller amounts of feces. For example, a relatively higher gas pressure causes a relatively higher shock.

Colon liquid rotation rate—a colon liquid rotation rate dislodges relatively larger amounts of feces and/or results in a faster rate of removal.

Agitator rotation rate—a higher axial rotation rate causes a higher colon liquid rotation rate.

Size of shredded fecal matter—a relatively small average particle size results in relatively higher cleaning rates and/or reduced risk of blocking the output conduit.

Systems for Maintaining Colon Fill Levels: Measuring Input/Output

Figure 8:
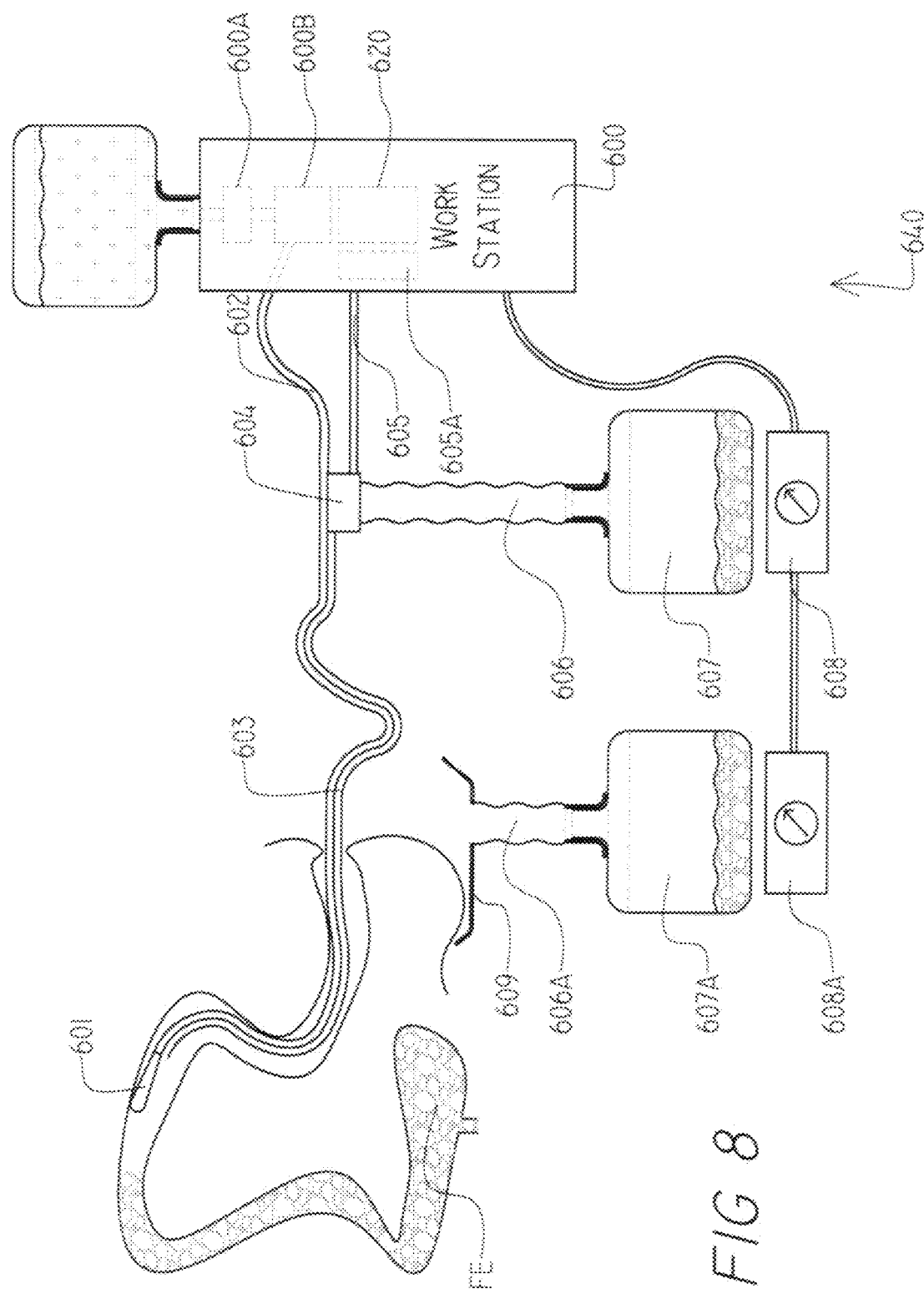
FIG. 8 is a simplified schematic of a system for controlling fluid input to a colon based on measurements of input and output flows of the system, according to some embodiments of the invention.

Attention is now drawn to FIG. 8, which presents a system for precision measuring of (a) fluids inserted into the body and (b) fecal matter and fluids coming out of the body, which is useful for striking a balance between the two, according to an embodiment of the present invention.

Device 640 (optionally built into an endoscope or mounted on an endoscope) has a tip 601 designed to be inserted into the body via the rectum. Workstation 600, using a pump 600A and a fluid meter 600B, supplies fluids via pipes 602 to the device tip 601. Fecal matter and fluids emerges from the body in two ways: (a) via the device's evacuation pipe 603 to fluids separator 604 and to draining pipe 606, or (b) via the rectum. For safety reasons, it is critically important to accurately estimate the amount of fluids within the body in real-time, for example to avoid introducing excessive fluids which might do bodily damage. Device 640 supplies this need.

Device 640 comprises Y junction 604. Junction 604 receives rotational power via a connector 605 from working station 600, which rotational power activates a helical apparatus within inserted cleaner 603, as taught above. Fluids and fecal matter transported by the helical apparatus to junction 604 is caused to drop down into draining pipe 606 and is prevented from entering connector 605. Fluids and fecal matter dropping down draining pipe 606 will reach a collection box 607 where it can be measured in real time using a scale 608. A similar procedure takes place for measuring fluid and fecal matter which appears in collector 609 after exiting spontaneously from the rectum.

Data from scales 608 and 608A and data from input pump 600A and fluid meter 600B within working station 600 can then be used in a simple subtractive calculation to determine in real-time how much fluid is housed within the patient colon in any given moment. This is important since overloading the patient's colon with water may be harmful.

In some embodiments, workstation 600 comprises a controller 620 which receives information from scales 608 and 608A and from fluid meter 600A, calculates an estimate of the amount of residual inserted fluid is currently in the colon, calculates a command based on this estimate, and sends that command to pump 600B, which then pumps a calculated amount of additional fluid into the colon so as to maintain an optimal operating environment for cleaning device 601.

Systems for Maintaining Colon Fill Levels: Measuring Water Levels

Figure 9A:
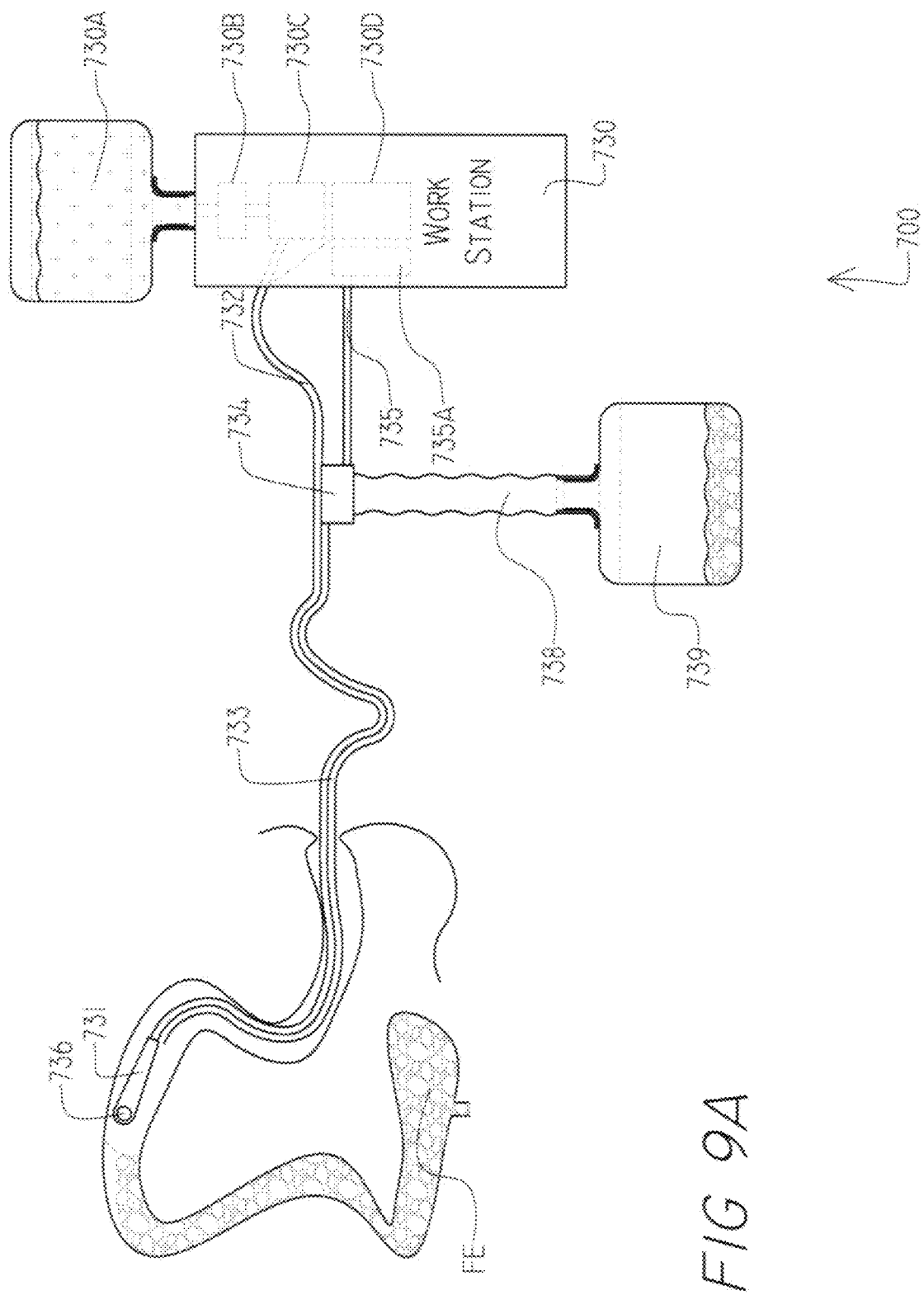

Attention is now drawn to FIG. 9A, which is a cleaning device 700 able to calculate a ratio of gaseous material to non-gaseous material (i.e. liquid, fecal matter or other solid) within a colon segment, in accordance with some embodiments of the invention.

Device 700 is a cleaning device similar to any of the cleaning devices discussed above. In particular device 700 may comprise an insertable portion 733 which comprises a helical rotating device as described above, powered by a rotating connector attached to a motor 735A in a workstation transmitting rotating motion through a connector 735. An operating tip 731 at a distal portion of insertable portion 733 comprises a sensor 736, which may be used to trigger an automatic response within workstation 730.

Sensor 736 provides information useable by a controller 730D to calculate commands to a water pump 730B for pumping water or any liquid. In some embodiments, workstation 730 comprises a controller 730D which receives information from sensor 736, uses that information to calculate an estimate of the amount of liquid needed to maintain an optimal operating environment for cleaning device 700, and calculates a command to pump 730B, commanding pump 730 to pump (or not pump) liquid accordingly.

In some embodiments sensor 736 is an ultrasound transducer which generates a signal that could tell the workstation (or show an operator) exactly the how much water or liquid, vs. air or other gas, surrounds tip 731 of the device. This procedure can yield precise information about the liquid concentration around tip 731, aiding system 700 (which may also use other sensors, such volume sensors, or flow meters and controllable pumps and scales as shown in FIG. 8), to supply an optimal amount of liquid to a lumen segment being cleaned.

In some embodiments sensor 736 senses and reports whether tip 731 is within water environment or within a gas environment. Several kinds of sensors can accomplish this task. For example, sensor 736 may comprise a module for measuring electric resistance around tip 731, Alternatively, sonic feedback could be used to determine material density around sensor 736.

Sensor 736 could be a colonoscope camera, or other camera. An image from such a camera could be processed by image processing software, and amounts of water in the intestine could be ascertained. Image processing software can also be used to examine the color of the light reaching the camera, to determine whether camera 736 is currently located in water (liquid) or in air or other gas. In some embodiments, signals received from sensor 736 are processed by controller 730D to run system 700 under algorithmic control. Sensor 736 enables system 700 to "know" whether there is an optimal amount of water in the colon, and to control pump 730B and rotational element 735 to achieve an optimal amount of water in the colon at the cleaning site. Alternatively, information derived from sensor 736 can be provided to a user, who then exercises manual control of operations of system 700, e.g. by increasing water flow by pushing a control button when he observes through a visualization modality that the distal tip of the cleaning device is out of the water.

Combinations

Elements in this section will be referenced according to FIG. 10, representing a non-limiting embodiment.

In some embodiments of the invention, there is more than one element as described herein. Non-limiting examples include; there may be more than one agitators 1014, more than one pulsing systems 1020, more than one input conduits 1012, more than one sensors 1022, more than one shredding apparatus 1018, more than one controller 1002 and/or more than one memory 1006.

In some embodiments of the invention, one type of element can serve as two or more elements as described herein. For example, rotational element 513 and/or 517 as described with reference to FIG. 2A can serve as an agitator 1014 and as a shredding apparatus 1018. For example, pulsing system 1020 can serve as an input conduit 1012, an agitator 1014 and/or as shredding apparatus 1018. For example, input 1012 conduit can also serve as output conduit 1010.

In some embodiments of the invention, one type of element can be external to the cleaning device, for example, as an external component optionally coupled to the cleaning device. For example, input conduit 1012 and/or output conduit 1010 can be in the form of a separate tube inserted from outside the body into the colon segment being cleaned.

Embodiments of the invention can include any combination or sub-combination of the above listed features and/or element. The embodiments described are not meant to limit the invention.

Experiments

Some of the embodiments presented above have been tested in in vivo animal experiments. A non-limiting example of an experiment is described:

Animal: each of 3 female pigs weighing 85-105 kg underwent 3 cleaning procedures separated by a week between the cleanings. The animals had partly prepared or unprepared colons.

Device: an experimental prototype, having an embodiment similar to that illustrated in FIG. 3D (including additional elements such as the shredding mechanism similar to that of FIG. 3A) was attached to a standard colonoscope and inserted into the colon via the anal sphincter.

Flow rates: fluid input and mixture (e.g., feces and/or fluid) output flow rates of between 500 cc/minute and 3000 cc/minute were tested.

Pulsing system: the fluid-fecal mixture inside the colon was agitated using alternating liquid/gas pulsed segments (e.g., as described in the section "Pulsing systems").

Rotational element: the fluid-fecal mixture inside the colon was agitated using a helical device (e.g., device 513 and/or 517) with applied rotational speeds of between 700 rpm and 7000 rpm. The induced rotation rate of the liquid in the liquid-filled colon was observed using a camera inside the colon segment.

Results: The colon segment in each of the pigs was visually inspected using the colonoscope, and was determined to be cleaned. Cleaning was achieved in unprepared and partly prepared colons.

Conclusion: Inserting fluid into the colon segment, agitating the fluid-fecal mixture inside the colon segment using the pulsing system and/or the rotational element, and removing the mixture provides satisfactory cleaning of the colon segment.

It is expected that during the life of a patent maturing from this application many relevant endoscopes and colonoscopes will be developed and the scope of the terms "endoscope" and "colonoscope" is intended to include all such new technologies a priori.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for cleaning a colon, comprising:
   inserting a fluid supply pipe into an anal canal opening at least 150 cm into the colon while a proximal end of the fluid supply pipe remains outside the colon;
   supplying fluid to the proximal end of the fluid supply pipe as a mix of liquid segments cyclically alternating with gas segments to be supplied to the colon, wherein said mix of liquid segments cyclically alternating with gas segments includes at least two liquid segments and at least two gas segments located in said fluid supply pipe simultaneously;
   wherein each of the gas segments is compressed in volume between a pair of liquid segments while traveling along the fluid supply pipe;
   wherein said supplying including supplying the mix of alternating liquid and gas segments in sequences in the fluid supply pipe; and
   producing pulsed shockwaves of gas segments exiting a distal end of the fluid supply pipe.

2. The method of claim 1, wherein said supplying fluid includes supplying fluid in short supply bursts of liquid cyclically alternating with short supply bursts of gas to be supplied to the colon.

3. The method of claim 1, wherein said supplying fluid includes supplying liquid segments cyclically alternating with gas segments at a speed of over 400 cc/min.

4. The method of claim 1, comprising:
   increasing pressure in said colon segment with the supplied mix of liquid segments and gas segments;
   sensing the increasing pressure, using a sensor in communication with a controller; and
   reducing the increased pressure, in response to communication from the sensor, by removal, under control of the controller, a portion of the supplied mix.

5. The method of claim 4, comprising selecting a value of at least one parameter of supplied mixture of gas and liquid segments; and
   wherein the at least one parameter comprises one or more of: a pressure of the pressurized mixture, a volume of pulses of liquid within the pressurized mixture, and a frequency of pulses of liquid within the pressurized mixture.

6. The method of claim 1, wherein the producing pulsed shockwaves comprises decompression of the gas segments upon exiting the fluid supply pipe.

7. The method of claim 6, wherein the compression is generated by a pressure of about 1000 mbar above atmospheric pressure.

8. The method of claim 6, wherein the compression is generated by a pressure of about 200 mbar above.

9. The method of claim 1, comprising immersing the distal end of the fluid supply pipe in a fluid mixture of liquid and fecal matter, while the gas segments exit the distal end; and
agitating the fluid mixture by the shockwaves upon their production within the fluid mixture.

10. The method of claim 9, comprising cyclically repeating the pulsed shockwaves; and
breaking down fecal matter omni-directionally through the fluid mixture using the repeated pulsed shockwaves.

11. The method of claim 9, comprising controlling a level of the fluid mixture in the colon while simultaneously evacuating the fluid mixture and supplying the fluid through the fluid supply pipe, so that a standing level of fluid mixture in the colon is maintained to a depth in which the distal end of the fluid supply pipe can be immersed to generate the shockwaves and agitate the fluid mixture.

12. The method of claim 11, wherein the controlling a level of the fluid mixture comprises adjusting a proportion of gas and liquid in the alternating segments.

13. The method of claim 1, comprising producing pulsed jets by the liquid segments exiting the supply pipe.

14. The method of claim 13, comprising cyclically repeating the pulsed jets; and
breaking down fecal matter directionally by directional impingement of the pulsed jets on the fecal matter.

15. The method of claim 14, comprising cyclically repeating the pulsed shockwaves along with the cyclically repeated pulsed jets; and
breaking down fecal matter omni-directionally using the repeated pulsed shockwaves while the pulsed jets break down fecal matter by directional impingement.

16. The method of claim 14, comprising, during the breaking down of fecal matter by directional impingement of the pulsed jets on the fecal matter, increasing a velocity of the liquid segments forming the pulsed jets by increasing a relative proportion of gas to liquid in the alternating segments.

17. A device for cleaning a body cavity comprising:
a fluid supply pipe, sized for insertion up to at least 170 cm into a body orifice leading to the body cavity while a proximal end of the fluid supply pipe remains outside the body; and
a mixing workstation, fluidically coupled to a proximal side of the fluid supply pipe, and configured to supply fluid for delivery to a segment of the body cavity being cleaned at a distal end of the fluid supply pipe, when the fluid supply pipe is inserted into the body cavity;
wherein the mixing workstation is configured to generate the flow of supplied fluid as liquid segments cyclically alternating with gas segments, including at least two liquid segments and at least two gas segments located in said fluid supply pipe simultaneously, wherein the mixing workstation is configured to supply the gas segments under compression; and
wherein said mixing workstation is configured to generate the simultaneous flow of the at least two liquid segments and at least two gas segments in sequence in the fluid supply pipe.

18. The device of claim 17, wherein mixing workstation is configured to supply the gas segments under compression so that expansion of the gas segments upon reaching the distal end of the fluid supply pipe produces shockwaves.

19. The device of claim 17, wherein the mixing workstation mixes the liquid and gas using the Venturi effect.

20. The device of claim 17, comprising a pressurized liquid source and a pressurized gas source coupled to the mixing workstation.

21. The device of claim 20, wherein the mixing workstation is configured to alternate supplying of liquid from the pressurized liquid source and supplying of gas from the pressurized gas source to generate the alternating liquid and gas segments, respectively.

22. The device of claim 17, wherein the mixing workstation comprises electrical valves, and is configured to operate the valves to produce the alternating liquid and gas segments.

23. The device of claim 22, wherein the mixing workstation operates the valves to produce a proportion of liquid and gas in the liquid and gas segments according to a preset of the mixing workstation.

24. The device of claim 23, wherein the preset specifies a flow rate of gas relatively larger than the flow rate of liquid.

25. The device of claim 24, wherein the preset specifies a proportion of about 80% gas.

26. The device of claim 17, comprising a material output tube configured to be inserted to the colon segment from the anal canal opening along with the fluid supply tube, and configured for removal through the material output tube of a fluid mixture from the colon segment comprising at least the supplied liquid, and fecal matter broken down by action of the supplied alternating liquid and gas segments.

27. The device of claim 26, comprising a controller and at least one sensor in communication with said controller, wherein said at least one sensor is configured to measure at least one of a rate of fluid flow and a pressure of the fluid mixture;
wherein said controller is configured to control, based on measurements from the at least one sensor:
supplying of the supplied fluid to the colon segment from said fluid supply pipe, and
control of removal of the fluid mixture from the colon segment via said material output tube;
wherein the gas segments are compressed so that expansion of the gas segments upon reaching the distal end of the fluid supply pipe produces shockwaves; and
wherein the controller is configured to control supplying of the supplied fluid and removal of the fluid mixture to maintain liquid of the fluid mixture at a standing depth within the colon sufficient to immerse the distal end of the fluid supply pipe, so that shockwaves generated by the gas exiting the fluid supply pipe are generated within the standing liquid, thereby agitating the fluid mixture.

28. The device of claim 27, wherein the controller is configured to control providing of the fluid through the fluid supply tube while maintaining a pressure within the colon within a preset range.

29. The device of claim 27, wherein the controller is configured to control a proportion of gas and liquid in the supplied fluid to maintain the standing depth.

30. A method of cleaning a colon segment of a patient, the method comprising:
administering into the colon segment a pressurized mixture of gas segments cyclically alternating with liquidd segments, wherein the cyclically alternating gas and liquid segments include at least two liquid segments and at least two gas segments located in the fluid supply pipe simultaneously, wherein the gas segments are compressed in volume while traveling along supply pipe, and wherein said administering includes supplying the mixture of alternating liquid and gas segments in sequence; the administering including;

transferring energy from the pressurized mixture to break down fecal matter in the colon segment, and increasing pressure in said colon segment with the administered pressurized mixture;

sensing the increasing pressure, using a sensor in communication with a controller; and reducing the increased pressure, in response to commmunication from the sensor, by removal of a portion of the pressurized mixture under control of the controller.

31. The method of claim 30, comprising selecting a value of at least one parameter of the administering the pressurized mixture of gas and liquid; and wherein the at least one parameter comprises one or more of: a pressure of the pressurized mixture, a volume of pulses of liquid within the pressurized mixture, and a frequency of pulses of liquid within the pressurized mixture.

* * * * *